United States Patent
Dissanayake et al.

(10) Patent No.: US 11,348,366 B2
(45) Date of Patent: May 31, 2022

(54) APPARATUS AND METHOD FOR DETERMINING COSMETIC SKIN ATTRIBUTES

(71) Applicant: The Procter & Gamble Company, Cincinnati, OH (US)

(72) Inventors: Dissanayake Mudiyanselage Mahathma Bandara Dissanayake, Singapore (SG); Naoki Miyamoto, Kobe (JP)

(73) Assignee: The Procter and Gamble Company, Cincinnati, OH (US)

( * ) Notice: Subject to any disclaimer, the term of this patent is extended or adjusted under 35 U.S.C. 154(b) by 244 days.

(21) Appl. No.: 16/856,336

(22) Filed: Apr. 23, 2020

(65) Prior Publication Data
US 2020/0342213 A1    Oct. 29, 2020

Related U.S. Application Data

(60) Provisional application No. 62/837,207, filed on Apr. 23, 2019.

(51) Int. Cl.
*G06V 40/16* (2022.01)
*G16H 50/30* (2018.01)
(Continued)

(52) U.S. Cl.
CPC ......... *G06V 40/171* (2022.01); *A45D 44/005* (2013.01); *A61B 5/0077* (2013.01);
(Continued)

(58) Field of Classification Search
CPC .... G06V 40/171; G06V 10/56; G06V 10/235; G16H 50/70; G16H 50/20; G16H 50/30;
(Continued)

(56) References Cited

U.S. PATENT DOCUMENTS 6,463,433 B1 * 10/2002 Baclawski .......... G06F 16/9014
707/999.005
6,571,003 B1    5/2003 Hillebrand et al.
(Continued)

FOREIGN PATENT DOCUMENTS

CN    104299011 A    1/2015
JP    2009082338 A    4/2009
(Continued)

OTHER PUBLICATIONS

Bargh, Becky, "Selfie skin analysis found to boost customer conversion by 50%", Retrieved from: https://www.cosmeticsbusiness.com/news/article_page/Selfie_skin_analysis_found_to_boost_customer_conversion_by_50/144771, Jul. 6, 2018, 3 Pages.
(Continued)

*Primary Examiner* — Prabodh M Dharia
(74) *Attorney, Agent, or Firm* — Alexandra S. Anoff

(57) ABSTRACT

A method of determining a cosmetic skin attribute of a person is provided. The method includes obtaining a color channel image of a person's skin, analyzing the color channel image with a computer using entropy statistics to obtain an entropy value, and then determining a cosmetic skin attribute for the person based on the entropy value.

14 Claims, 14 Drawing Sheets

(51) Int. Cl.
    *G16H 50/70* (2018.01)
    *G16H 50/20* (2018.01)
    *A45D 44/00* (2006.01)
    *A61B 5/00* (2006.01)
    *A61B 5/103* (2006.01)
    *G06V 10/56* (2022.01)
    *G06V 10/22* (2022.01)
    *G06F 3/0488* (2022.01)

(52) U.S. Cl.
    CPC ............ *A61B 5/1032* (2013.01); *A61B 5/442* (2013.01); *A61B 5/443* (2013.01); *A61B 5/445* (2013.01); *A61B 5/726* (2013.01); *A61B 5/7257* (2013.01); *A61B 5/7267* (2013.01); *A61B 5/748* (2013.01); *A61B 5/7435* (2013.01); *G06V 10/235* (2022.01); *G06V 10/56* (2022.01); *G16H 50/20* (2018.01); *G16H 50/30* (2018.01); *G16H 50/70* (2018.01); *A45D 2044/007* (2013.01); *A61B 2576/02* (2013.01); *G06F 3/0488* (2013.01); *G06V 40/178* (2022.01)

(58) Field of Classification Search
    CPC .. A45D 44/005; A61B 5/0077; A61B 5/1032; A61B 5/442; A61B 5/443; A61B 5/445; A61B 5/7257; A61B 5/726; A61B 5/7267; A61B 5/7435; A61B 7/748
    USPC ............ 345/594; 382/128, 254; 700/999.005
    See application file for complete search history.

(56) References Cited

U.S. PATENT DOCUMENTS

| | | | |
|---|---|---|---|
| 9,111,132 B2 | 8/2015 | Aoki | |
| 9,665,945 B2 | 5/2017 | Wang | |
| 9,747,685 B2 | 8/2017 | Miyamoto | |
| 2006/0228037 A1* | 10/2006 | Simon | G06V 40/162 382/254 |
| 2008/0080755 A1* | 4/2008 | Payonk | A61B 5/0059 382/128 |
| 2009/0080727 A1 | 3/2009 | Cotton et al. | |
| 2010/0158330 A1* | 6/2010 | Guissin | A61B 5/444 382/128 |
| 2010/0284610 A1 | 11/2010 | Yoshikawa | |
| 2011/0286643 A1* | 11/2011 | Kislal | G06V 40/10 382/128 |
| 2017/0270593 A1 | 9/2017 | Sherman | |
| 2018/0350071 A1 | 12/2018 | Purwar | |
| 2019/0377969 A1* | 12/2019 | Kuo | G06Q 30/0282 |
| 2020/0170564 A1* | 6/2020 | Jiang | A61B 5/441 |
| 2020/0342594 A1* | 10/2020 | Dissanayake | G16H 30/40 |

FOREIGN PATENT DOCUMENTS

| | | |
|---|---|---|
| KR | 100408829 B1 | 1/2004 |
| KR | 101701210 B1 | 2/2017 |

OTHER PUBLICATIONS

AA01346M PCT Search Report and Written Opinion for PCT/US2020/029423 dated Sep. 29, 2020, 18 pages.

"The Revieve Digital Skincare Advisor", Retrieved from: https://www.youtube.com/watch?v=OuBWSSO0mNk, Sep. 9, 2017, 1 Page.

"VISIA Redefining the Vision of Skin Care", Retrieved from: https://www.canfieldsci.com/imaging-systems/visia-complexion-analysis/, Retrieved Date: May 6, 2021, 10 Pages.

All Office Actions; U.S. Appl. No. 16/856,305.

* cited by examiner

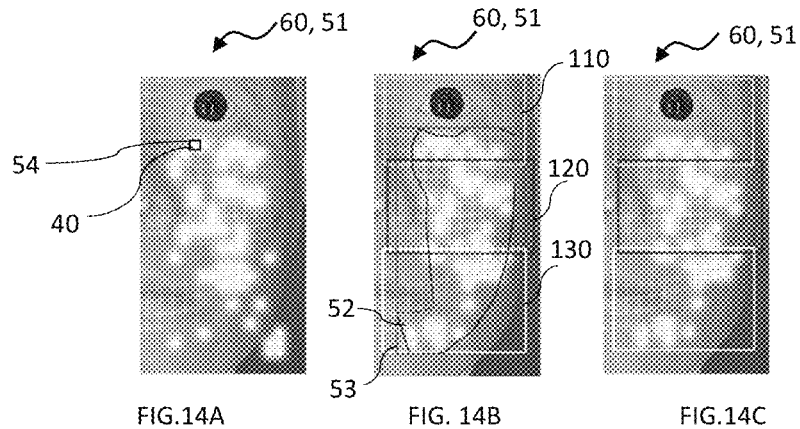
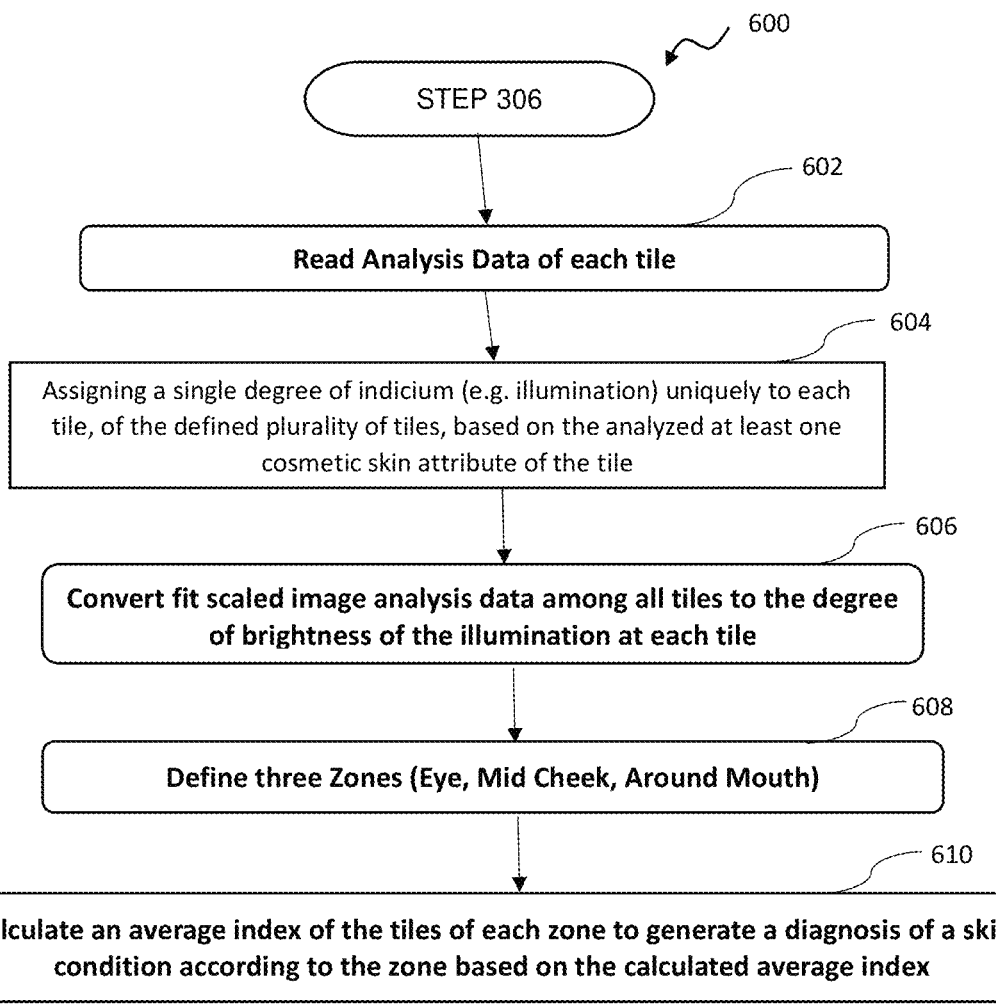
FIG. 15

US 11,348,366 B2

APPARATUS AND METHOD FOR DETERMINING COSMETIC SKIN ATTRIBUTES

TECHNICAL FIELD

The present invention relates to an apparatus and method for determining cosmetic skin attributes.

BACKGROUND

Skin imaging methods have been widely used to study different phenotypes of skin aging. Numerous image analysis techniques and algorithms have been proposed in literature to characterize aging skin particularly focusing on aging phenotypes such as wrinkles, spots and sagging. It is known that appearance of skin aging related phenotypes is a continuous process over time. For example, uneven pigmentation may first cause visually imperceivable spots, which eventually may become visible over time. As such, a younger consumer (e.g., less than 30 years of age) generally does not have classic visible skin aging related phenotypes and therefore has the impression that there are no pressing needs to prevent, delay, and/or mitigate such visibly imperceivable phenotypes of aging, until it is too late.

U.S. Publication Number 2010/0284610A1 ("the '610 Publication") relates to a skin color evaluation method for evaluating skin color from an input image including a face region. The '610 Publication describes dividing a face region of the image into predetermined regions according to first feature points formed of at least 25 areas that are set beforehand and second feature points that are set by using the first feature points. The '610 Publication further describes performing a skin color distribution evaluation by generating a skin color distribution based on average values using at least one of $L^*$, $a^*$, $b^*$, $C_{ab}^*$, and $h_{ab}$ of a $L^*a^*b^*$ color system, tri-stimulus values X, Y, Z of an XYZ color system and the values of RGB, hue H, lightness V, chroma C, melanin amount, and hemoglobin amount, followed by performing evaluation based on measured results with respect to the regions that are divided and displaying the measured results or evaluation results on a screen. However, the '610 Publication is focusing on visible skin color distribution and it fails to describe skin aging related phenotypes, and therefore does not describe any method for evaluating visually imperceivable skin aging related phenotypes.

Accordingly, there is a need for a method for determining cosmetic skin attributes of a person so as to enable proactive skincare treatment at an earlier stage.

SUMMARY OF THE INVENTION

The present invention relates to a method of determining a cosmetic skin attribute of a person, the method comprising the steps of:
 a) obtaining at least one color channel image comprising at least one portion of skin of the person;
 b) analyzing the at least one color channel image using entropy statistics to obtain an entropy value; and
 c) determining the cosmetic skin attribute of the at least one portion of skin of the person based on the entropy value.

BRIEF DESCRIPTION OF THE DRAWINGS

FIGS. 14A to 14C are process flow diagrams illustrating a process of displaying the plurality of tiles according to the present invention;

FIG. 15 is a flow chart illustrating a process of displaying the plurality of tiles according to the present invention;

DETAILED DESCRIPTION

Figure 1:
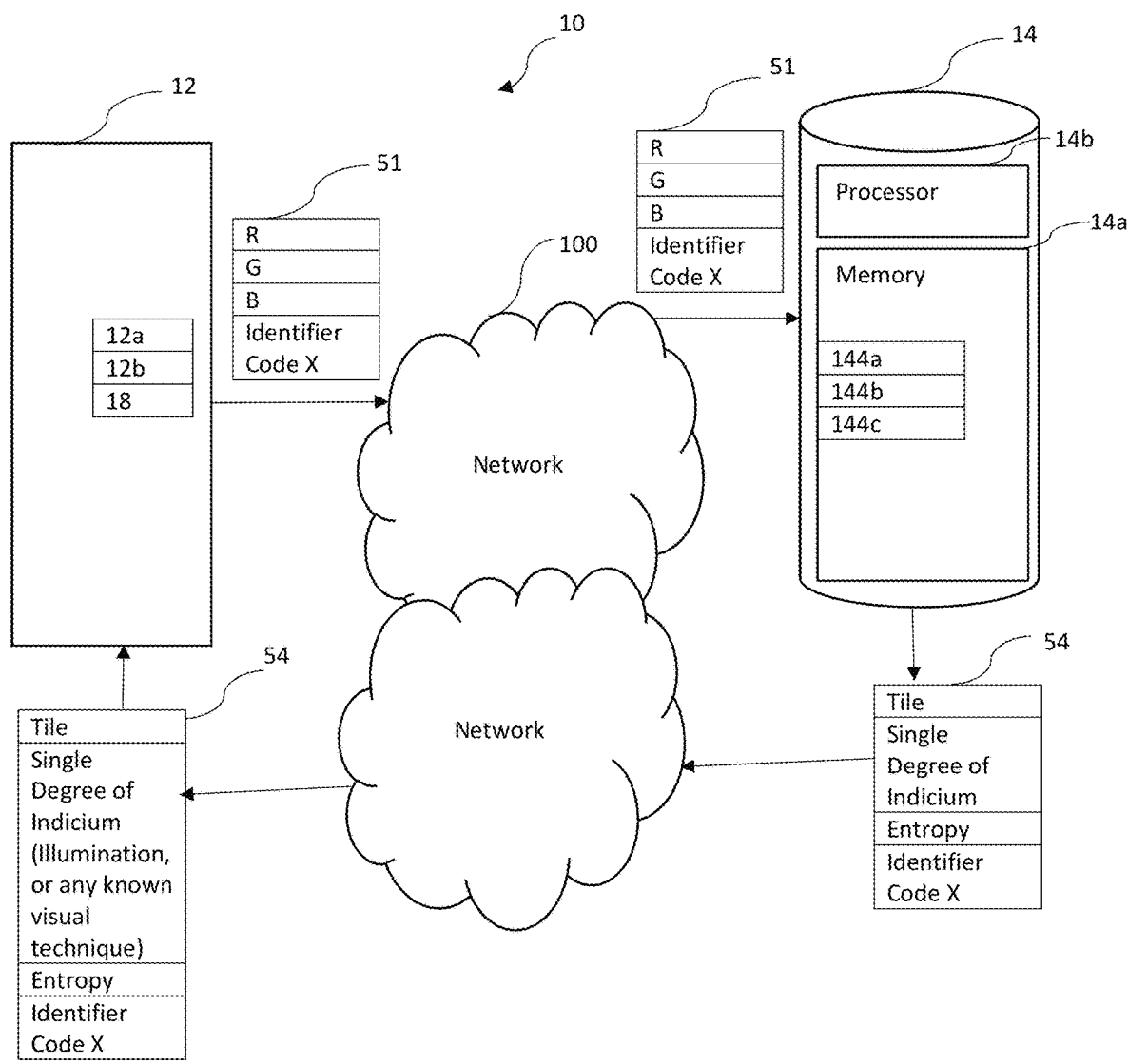
FIG. 1 is a diagram illustrating an exemplary system for determining a cosmetic skin attribute over a network according to the present invention.

It is known that when the skin is subjected to stress (caused by UV, aging, mental, environmental factors), skin will be damaged at various levels including DNA level, cellular level and tissue level. Such damages to the skin can result in skin imperfections. Presence of these skin imperfections significantly impact on optics of the skin such as described in the following examples:

- If the stratum corneum is dry (winter/air condition), light will reflect more from the surface (surface reflection) enhancing skin micro texture which cause lines on the skin
- If the dermis is damaged (UV), less light will scatter at dermis (also known as dermis-scattering) and light will penetrate skin (less subsurface reflection). When there is less demis-scattering, and the skin appears darker as a result.
- If skin is exposed to chronic UV, skin produces more melanin. Melanin absorbs light reducing subsurface reflection and hence skin appears darker.

The above skin imperfections manifest as visually imperceivable signals of poor skin quality to the consumers eye. Consumers may consider these imperfections as impurities at a subconscious level, but are not able to take action to improve the imperfections because of lack of conscious knowledge. If the skin is subject to chronic stress and/or untreated, these visually imperceivable impurities may eventually lead to visible and perceivable phenotypes (pigmented spots, wrinkles, sagging).

The present invention relates to a method, apparatus and system for determining at least one cosmetic skin attribute of a subject and a graphical user interface. The method comprises the steps of (a) obtaining at least one color channel image comprising at least one portion of skin of the person; (b) analyzing the at least one color channel image using entropy statistics to obtain an entropy value; and (c) determining the cosmetic skin attribute of the at least one portion of skin of the person based on the entropy value.

It has been surprisingly found that entropy values obtained by analyzing a color channel image comprising at least one portion of skin of a person can be used determine cosmetic skin attributes that are visually perceivable as well as visually imperceivable cosmetic skin attributes.

As explained below, if a cosmetic skin attribute of a person can be determined based on an entropy value that is obtained by analyzing a color channel image comprising at least one portion of skin of a person using entropy statistics, useful information can be inferred (e.g. condition of the cosmetic skin attribute) so that the person can seek proactive skincare treatment to improve the condition of the cosmetic skin attribute. Specifically, as described hereinafter, a color channel image having at least one portion of skin of a person may have a region of interest on the at least one portion of skin that is having a lower entropy value relative to other regions of interest. A lower entropy value in the region of interest shows less intensity variation which is indicative of a better cosmetic skin attribute condition. Accordingly, a higher entropy value in other regions of interest show more intensity variation which is indicative of a poorer cosmetic skin attribute condition. A further advantage is that the proactive skincare treatment can be targeted to a specific region of interest.

Prior to describing the present invention in detail, the following terms are defined and terms not defined should be given their ordinary meaning as understood by a skilled person in the relevant art.

"Entropy" as used herein refers to a Shannon entropy (E) of a discrete random distribution (p(x)) and is defined by the following equation:

$$E(p) = -\sum_{x} p(x) \times \log p(x) \quad (1)$$

wherein p(x) is the distribution of grey levels

E(p) represents the amount of information in a digital image or a color channel image in a color system after conversion of the digital image to the color channel image. "Entropy statistics" as used herein refers to a statistical method that uses entropy as a descriptive statistic for analyzing digital images or color channel images. In a non-limiting example wherein the digital image is an RGB image, entropies (entropy values) for each R (red), G(green) and B(blue) channel can be calculated separately. The entropy value of an image can be calculated by calculating at each pixel position (i,j) the entropy value of the pixel-values within a 2-dimensional region centered at (i,j). The 2-dimensional region may be a part of a color channel image. Programming software packages such as Python may be used to calculate the entropy value.

"Cosmetic skin attribute" as used herein includes all skin attributes that provide a visual/aesthetic effect on an area of the human body or impact skin appearance and/or feel. Some non-limiting examples of a cosmetic skin attribute may include skin purity, skin age, skin topography, skin tone, skin pigmentation, skin pores, skin inflammation, skin hydration, skin sebum level, acne, moles, skin radiance, skin shine, skin dullness, uneven tone, or skin barrier. It will be appreciated by a skilled person that the above cosmetic skin attributes are standard terms, and a corresponding definition of the cosmetic skin attribute may be found in the following published references namely, "Handbook of cosmetic science and technology, $3^{rd}$ edition, editors Andre O. Barel, Marc Pave, Howard I. Maiback, CRC Press, 2009", "Cosmetic Science and Technology-Theoretical Principles and Applications, editors Kazutami Sakamoto Robert Y. Lochhead, Howard I. Maibach, Yuji Yamashita, Elsavier, 2017", "Cosmetic Dermatology: Products and Procedures, Editor(s): Zoe Diana Draelos, Blackwell Publishing Ltd, 2010". Cosmetic skin attributes do not include skin attributes related to medical conditions or underlying medical conditions.

"Imperceivable cosmetic skin attribute" as used herein refers to a cosmetic skin attribute that cannot be perceived or is imperceptible by the perceiver, i.e. a person, a user, or a human subject. Perceive derives from the word "Perception" which refers to the organization, identification, and interpretation of sensory information in order to represent and understand the presented information, or the environment. All perception involves signals that go through the nervous system, which in turn result from physical or chemical stimulation of the sensory system. For example, vision involves light striking the retina of the eye, smell is mediated by odor molecules, and hearing involves pressure waves. Perception is not only the passive receipt of these signals, but it is also shaped by the recipient's learning, memory, expectation, and attention. Perception can be split into two processes, i.e. process (1) that relates to processing the sensory, input, which transforms these low-level information to higher-level information (e.g., extracts shapes for object recognition), and process (2) that relates processing which is connected with a person's concepts and expectations (or knowledge), restorative and selective mechanisms (such as attention) that influence perception. For example, a perceiver may see an object in process (1) but does not have the knowledge to perceive and recognize what the object represents/mean in process (2), and therefore may regard the object to be visually imperceivable.

"Visually imperceivable cosmetic skin attribute" as used herein includes all cosmetic skin attributes which are not detectable by an unaided eye or a cosmetic skin attribute detectable visually by a consumer but the consumer does not understand the cosmetic skin attribute, and therefore regarded as imperceivable cosmetic skin attributes. Some nonlimiting examples of a visually imperceivable cosmetic skin attribute that is not detectable visually by the unaided eye include cosmetic skin inflammation, skin sebum level, or any underlying cosmetic skin attribute.

"Unaided" as used herein means without assistance from diagnostic equipment.

"Tile" as used herein includes a unit, such as for example a pixel, that form a part of a digital image and accordingly "Tiles" form the whole of the digital image.

"Digital image data" as used herein includes image data obtained from an image obtaining device including but not limited to a digital camera, a photo scanner, a computer readable storage medium capable of storing digital images, and any electronic device including picture taking capabilities. Digital image data may also include color channel images which are converted from a RGB image into a color channel image in a color system.

"Single degree of indicium" as used herein includes all electronic visual representations including but not limited to a graphical symbol, a numerical value, a color code, illumination techniques and combinations thereof.

"Skin Attribute Index" as used herein refers to a score that can be calculated based on a mathematical formula or a model derived from statistical methods and data or a lookup table (an array of information). The Skin Attribute Index may be generated as a probability value indicative of a condition of the cosmetic skin attribute of the at least one portion of skin of the person relative to a defined population of people, preferably the Skin Attribute Index is generated as a function of the entropy value defined by F(Entropy Value), wherein said function is determined by a model established upon a training dataset wherein the training dataset comprises: (i) a plurality of color channel images of a the defined population of people, wherein each of the plurality of color channel images comprises facial skin of a person in the defined population of people, wherein the facial skin comprises the cosmetic skin attribute; (ii) an associated class definition based on the cosmetic skin attribute.

"L*a*b*" as used herein, refers to the commonly recognized color space specified by the International Commission on Illumination ("CIE"). The three coordinates represent (i) the lightness of the color (i.e., L*=0 yields black and L*=100 indicates diffuse white), (ii) the position of the color between magenta and green (i.e. negative a*values indicate green while positive a*values indicate magenta) and (iii) the position of the color between yellow and blue (i.e. negative b*values indicate blue and positive b*values indicate yellow).

"Chromophore mapping" as used herein, refers to the commonly recognized chromophore space for melanin and hemoglobin mapping and determining melanin or hemoglobin concentration which may be used as an indicator of overall skin tone. Mean melanin or hemoglobin may be calculated from the chromophore map data. Additionally, skin tone evenness can be determined by melanin or hemoglobin evenness (e.g. standard deviation) which also may be calculated from the chromophore map data.

"Skin purity" as used herein, appearance of the absence of skin imperfections in at least of portion of skin of a person. The skin imperfections include cosmetic skin attributes which impact irregular or non-uniform spectral properties composed of the surface reflection of the skin topographical morphology and/or the sub-surface reflection of skin chromophores such as melanin, haemoglobin and/or keratinocyte and fibroblast oriented cellular metabolites, and include but are not limited to skin radiance, skin tone or the like.

"Skin age" as used herein, means apparent age which refers to the age of skin of a person that is visually estimated or perceived to be, compared to norm age skin appearances, based on the physical appearances, preferably a face of the person, preferably at least a portion of a face of the person, more preferably, at least one region of interest (ROI) of the at least a portion of a face of the person, even more preferably, the at least one ROI is selected from the group consisting of: a skin region around the eye ("eye region"), a skin region around the cheek ("cheek region"), a skin region around the mouth ("mouth region"), and combinations thereof.

"Skin tone" as used herein, generally refers to the overall appearance of basal skin color or color evenness. Skin tone is typically characterized over a larger area of the skin. The area may be more than 100 mm2, but larger areas are envisioned such as the entirety of the facial skin or other bodily skin surfaces (e.g. arms, legs, back, hands, neck).

"Skin wrinkle" as used herein, generally refers to a fold, ridge or crease in the skin and includes but is not limited to fine lines, super fine lines, fine wrinkles, super fine wrinkles, wrinkles, lines. Skin wrinkle may be measured in terms of, for example, density and/or length.

"Skin radiance" as used herein, generally refers to an amount of light that the skin reflects, and may be referred to as skin shine.

"Skin texture" as used herein, generally refers to the topology or roughness of the skin surface.

"Skin tension" as used herein, generally refers to the firmness or elasticity of the skin.

"Skin sebum level" as used herein, generally refers to an amount of sebum which is an oily or waxy matter secreted by sebaceous glands in the skin.

"Skin spots" as used herein, generally refers discoloration or uneven pigmentation (e.g hyperpigmentation, blotchiness) of the skin. Skin spots may be evaluated in terms of, e.g. density, size, and/or degree of discoloration.

"Skin care product" as used herein, refers to a product that includes a skin care active and regulates and/or improves skin condition.

"Digital image" as used herein, refers to a digital image formed by pixels in an imaging system including but not limited to standard RGB, or the like and under images obtained under different lighting conditions and/or modes. Non-limiting examples of a digital image include color images (RGB), monochrome images, video, multispectral image, hyperspectral image or the like. Non-limiting light conditions include white light, blue light, UV light, IR light, light in a specific wavelength, such as for example light source emitting lights from 100 to 1000 nm, from 300 to 700 nm, from 400 to 700 nm or different combinations of the upper and lower limits described above or combinations of any integer in the ranges listed above. The digital image may be obtained from an image obtaining device including but not limited to a digital camera, a photo scanner, a computer readable storage medium capable of storing digital images, and any electronic device including picture taking capabilities.

In the following description, the method described is a method for determining a cosmetic skin attribute. Accordingly, the apparatus described is an apparatus for determining a cosmetic skin attribute. The apparatus may also be configured for generating for display, on a display, entropy statistics of digital image data of at least a portion of a face of a subject, and the graphical user interface described is a graphical user interface for displaying entropy statistics of the digital image data of at least a portion of a face of the subject. The system described is an entropy-based system for determining a cosmetic skin attribute. In an exemplary embodiment, the system is a stand-alone imaging system (shown in FIG. 2) that is located at a retail cosmetics counter for the purpose of analyzing and recommending cosmetic and skin care products. However, it is contemplated that the system and the method may be configured for use anywhere, such as for example as shown in FIG. 1, through an electronic portable device comprising an image obtaining unit/device and a display, wherein the electronic portable device is connected to an apparatus for generating for display on a display, a graphical user interface for visualizing entropy value of a cosmetic skin attribute through a network.

FIG. 1 is a schematic diagram illustrating a system 10 for visualizing a cosmetic skin attribute according to the present invention. The system 10 may include a network 100, which may be embodied as a wide area network (such as a mobile telephone network, a public switched telephone network, a satellite network, the internet, etc.), a local area network (such as wireless-fidelity, Wi-Max, ZigBee™, Bluetooth™, etc.), and/or other forms of networking capabilities. Coupled to the network 100 are a portable electronic device 12, and an apparatus 14 for generating for display on a display, a graphical user interface for visualizing a cosmetic skin attribute. The apparatus 14 is remotely located and connected to the portable electronic device through the network 100. The portable electronic device 12 may be a mobile telephone, a tablet, a laptop, a personal digital assistant and/or other computing device configured for capturing, storing, and/or transferring a digital image such as a digital photograph. Accordingly, the portable electronic device 12 may include an input device 12a for receiving a user input, an image obtaining device 18 such as a digital camera for obtaining images and an output device 12b for displaying the images. The portable electronic device 12 may also be configured for communicating with other computing devices via the network 100. The portable electronic device 12 may further comprise an image processing device (not shown) coupled with said imaging obtaining device 18 for analyzing the obtained at least one color channel image using entropy statistics to obtain an entropy value and determining the cosmetic skin attribute of the at least one portion of skin of the person based on the entropy value. The image processing device preferably comprises a processor with computer-executable instructions. The portable electronic device 12 may further comprise a display generating unit (not shown, such as an electronic LED/LCD display) for generating a display to display content data describing the determined cosmetic skin attribute.

The apparatus 14 may include a non-transitory computer readable storage medium 14a (hereinafter "storage medium"), which stores image obtaining logic 144a, image analysis logic 144a and graphical user interface (hereinafter "GUI") logic 144c. The storage medium 14a may comprise random access memory (such as SRAM, DRAM, etc.), read only memory (ROM), registers, and/or other forms of computing storage hardware. The image obtaining logic 144a, image analysis logic 144b and the GUI logic 144c define computer executable instructions. A processor 14b is coupled to the storage medium 14a, wherein the processor 14b is configured to, based on the computer executable instructions, for implementing a method 90 for determining a cosmetic skin attribute of a subject according to the present invention as described herein after with respect to the block diagram of FIG. 4 and the flowchart of FIG. 5. The cosmetic skin attribute may be a visually imperceivable cosmetic skin attribute, wherein the visually imperceivable cosmetic skin attribute is a cosmetic skin attribute which is not detectable by an unaided eye, or a cosmetic skin attribute detectable visually by a consumer but the consumer does not understand the cosmetic skin attribute. An advantage of determining visually imperceivable cosmetic skin attributes is to enable consumers to make informed decisions and take pro-active action to improve the condition of the visually imperceivable cosmetic skin attributes.

Determination Method

Figure 4:
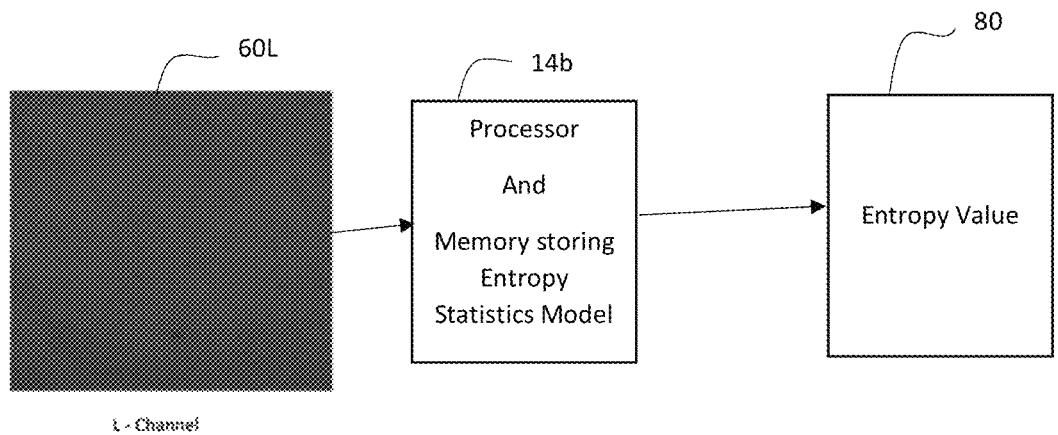
FIG. 4 is a block diagram illustrating a method for determining a cosmetic skin attribute according to the present invention.
Figure 5:
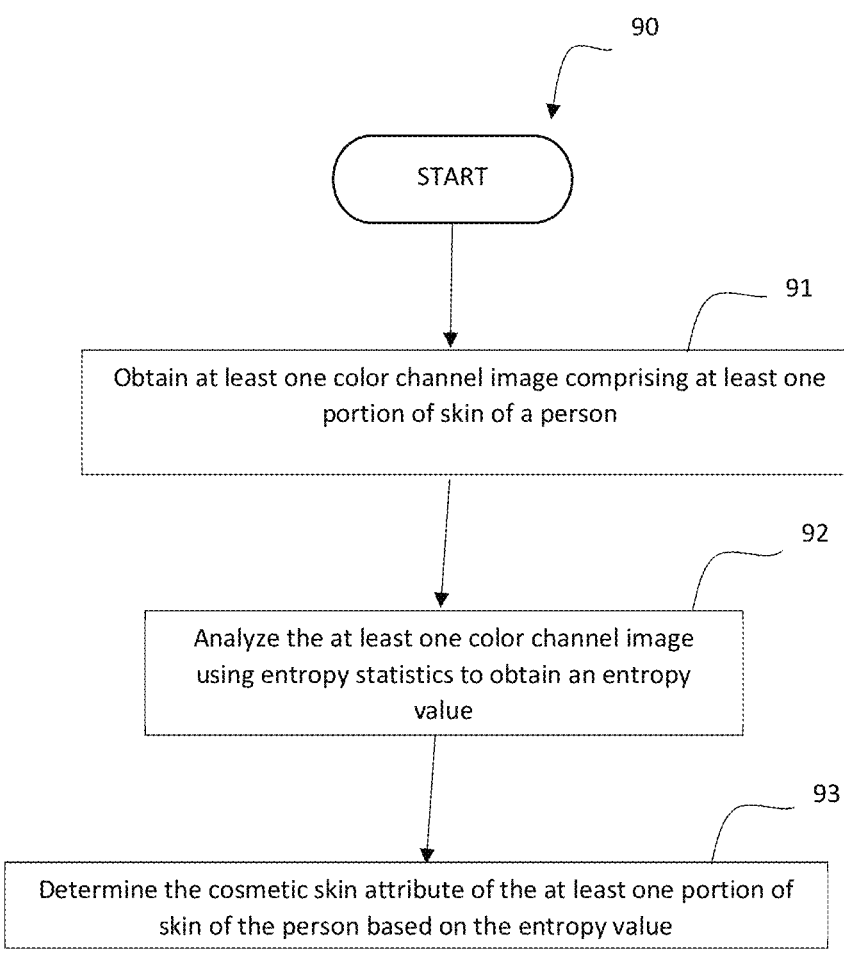
FIG. 5 is a flow chart illustrating a method for determining a method for determining a cosmetic skin attribute according to the present invention.
Figures 6A, 6B, 6C:
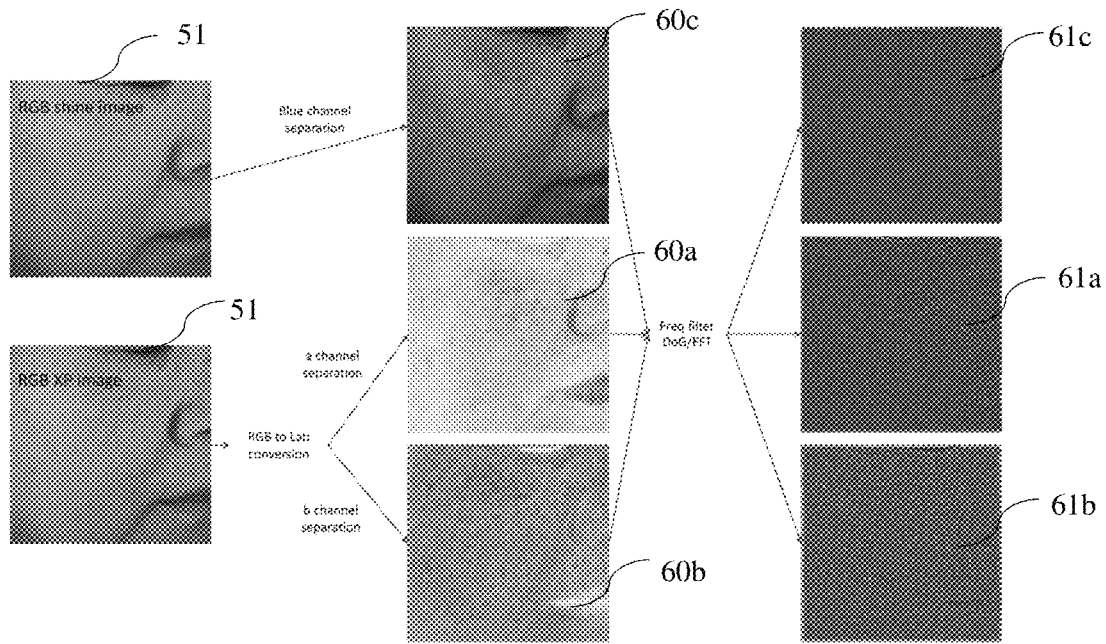
FIGS. 6A to 6C are a series of process flow diagrams illustrating a method for determining a cosmetic skin attribute according to the present invention.
Figure 7:
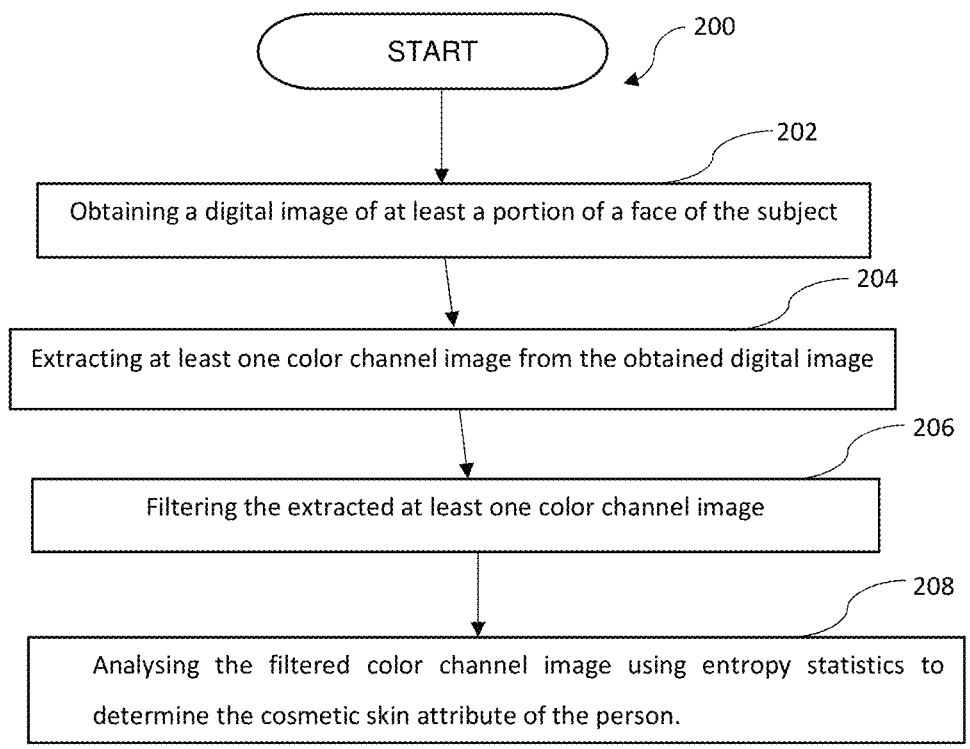
FIG. 7 is a flow chart illustrating a method for determining a cosmetic skin attribute according to the present invention.

Referring to FIGS. 4 and 5, when the processor 14b is initiated, the processor 14b causes at least one color channel image 60L comprising at least one portion of skin of the person to be obtained in step 91, e.g. via conversion of a digital image into a color channel image in a color system which will be described hereinafter with reference to FIGS. 6A, 6B, 6C and 7. The at least one color channel image 60L is analyzed in step 92 using entropy statistics to obtain an analysis output 80 wherein the analysis output 80 comprises an entropy value. In step 93, the cosmetic skin attribute of the at least one portion of skin of the person is determined based on the entropy value.

At least one color channel image may be an image in a color system selected from the group consisting of L*a*b* color system, RGB color system, HSL/HSV color system, and CMYK color system.

Table 1 below sets out each entropy value with a corresponding color channel image and corresponding cosmetic skin attributes to be determined based on the entropy value. The color channel image described in Table 1 is an image in the L*a*b* color system selected from the group consisting of a L channel image, an a-channel image, a b-channel image, a c-channel image, and combinations thereof.

TABLE 1

| Color Channel Image | Entropy Value | Cosmetic Skin Attribute |
| --- | --- | --- |
| L channel image | L-entropy value | skin purity, skin tone, skin radiance |
| a-channel image | a-entropy value | skin inflammation |
| b-channel image | b-entropy value | skin pigmentation or skin dullness |
| c-channel image | c-entropy value | Skin topography, including but not limited to pores, wrinkles, fine lines, sagging, skin elasticity and combinations thereof. |

Determining the cosmetic skin attribute may comprise generating a Skin Attribute Index as a probability value indicative of a condition of the cosmetic skin attribute of the at least one portion of skin of the person relative to a defined population of people. Specifically, in a visual perception study, consumers may be asked to rank digital images (e.g. photographs) of the defined population of people for a cosmetic skin attribute based on a predetermined scale. The ranked digital images may be stored as a database so as to be analyzed according to the method 90 to determine an entropy value that has the highest correlation with the cosmetic skin attribute.

Alternatively, the Skin Attribute Index may be generated as a function of the entropy value defined by a function, F(Entropy Value), wherein said function is determined by a model established upon a training dataset. The training dataset may comprise: (i) a plurality of color channel images of a defined population of people, wherein each of the plurality of color channel images comprises facial skin of a person in the defined population of people, wherein the facial skin comprises the cosmetic skin attribute; (ii) an associated class definition based on the cosmetic skin attribute. Techniques for building training datasets are known to a person skilled in the field of image processing methods and will not be further described.

The model may be a regression model or a classification model, preferably a linear regression model, more preferably a machine learning linear regression model, most preferably a machine learning support vector regression (SVR) model. The SVR model is a specific example of a Support Vector Machine (SVM) model. A machine learning model may also be a support vector classification model or a random forest regression model.

Using a SVR model enables the advantages of accuracy, reproducibility, speed in the performance of the method when implemented as a native application on a portable electronic device. In particular, the weight of a SVR model allows the native application to have a smaller hardware footprint, and consequently the methods according to the present invention may be easily deployed in portable electronic devices such as mobile phones with mobile phone operating systems (OS) including but not limited to iOS for the Apple™ phone or Android OS for Android phones.

The classification model may be used to classify consumers into a plurality of groups, each group having different degrees of a condition of the same cosmetic skin attribute, preferably two groups, more preferably three groups so as to define an associated class definition based on the numerical value of the Skin Attribute Index. For example, the method may display a heat map configured to classify regions of the skin into a high level of a cosmetic skin attribute condition or a low level of a cosmetic skin attribute condition based on thresholds assigned to each of the groups.

The at least one color channel image is an image in the L*a*b* color system selected from the group consisting of a L color channel image, an a-channel image, a b-channel image and a c-channel image from RGB color system, and combinations thereof; wherein the entropy value is selected from the group consisting of a L-entropy value, an a-entropy value, a b-entropy value, a c-entropy value, and combinations thereof; and wherein the function has the following formula:

Skin Attribute Index=$A+B\times(L$-entropy value)+
$C\times(a$-entropy value)+$D\times(b$-entropy value)+
$E\times(c$-entropy), wherein A, B, C, D, and E are constants; wherein at least one of B, C, D, and E is not 0.

It will be appreciated that the constants A, B, C, D, and E may vary based on the size and content of the training dataset, and may be any numerical value generated by the model based on the training dataset.

Specifically, each one of the entropy values above may be used alone or in combination with another one of the entropy values. For example using a single entropy value may result in faster computing speed which enables small devices with very basic hardware to be used, thereby resulting in a more efficient and cost effective product.

The at least one color channel image may be a L channel image; wherein the entropy value is a L-entropy value; wherein C, D, E each has a value of 0; and wherein the generated Skin Attribute Index is indicative of skin purity, skin tone or skin radiance.

It is known that when the skin is subjected to stress (caused by UV, aging, mental, environmental factors), skin will be damaged at various levels including DNA level, cellular level and tissue level. Such damages to the skin can result in skin imperfections. Presence of these skin imperfections significantly impact on optics of the skin such as described in the following examples:

If the stratum corneum is dry (Winter/Air condition), light will reflect more from the surface (surface reflection) enhancing skin micro texture which cause lines on the skin If the dermis is damaged (UV), less light will scatter at dermis (also known as dermis-scattering) and light will penetrate skin (less subsurface reflection). When there is less demis-scattering and hence skin appear darker.

If skin is exposed to chronic UV, skin produces more melanin. Melanin absorbs light reducing subsurface reflection and hence skin appear darker.

The above skin imperfections manifest as imperceivable signals of skin quality to the consumers eye. Consumers may consider these imperfections as impurities, but are not able to take action to improve the imperfections because of lack of knowledge. If the skin is subject to chronic stress and/or untreated, these imperceivable impurities may eventually lead to visible and perceivable phenotypes (pigmented spots, wrinkles, sagging).

It has been surprisingly found that a L-entropy value of a L color channel image has the highest correlation to skin purity.

A technical effect of selecting L-channel image as the at least one color channel image for a analyzing step to obtain a L-entropy value and to determine skin purity based on the L-entropy value according to methods according to the present invention is because L-entropy value has the highest correlation (r=0.89) to skin purity relative to other entropy values based on analyzing the color channel images. Below is data generated based on correlation with results from a visual perception study using statistical analysis using Pearson correlation coefficient (r). The correlation results are shown below in Table 2 below.

TABLE 2

| Entropy Value | Pearson Correlation Coefficient (r) with results of Visual Perception Study |
|---|---|
| L-entropy value | 0.89 |
| a-entropy value | 0.55 |
| b-entropy value | 0.7 |
| c-entropy value | 0.76 |

A higher Pearson correlation coefficient (r) means that the entropy value is a factor that contributes more to the condition of the cosmetic skin attribute that is studied in the visual perception study. Specifically, the visual perception study is conducted based on a predetermined number of panelists=302, age of the panelists=20-50. The panelists are asked rank photographs of people for skin purity (as an example of the cosmetic skin attribute) on a scale of 1 to 5. Based on the visual perception study results and above correlation results, it has been found that L channel entropy value of the filtered image (by frequency filter) has the highest correlation with the skin purity attribute. Therefore, use of the L-entropy value of the L channel to determine skin purity of at least a portion of skin of a person in a digital image can be used to transform skin purity from a visually imperceivable cosmetic skin attribute into an explainable cosmetic skin attribute in a consumer relevant way to consumers.

The at least one color channel image may be an a-channel image; wherein the entropy value is an a-entropy value;

wherein B, D, E each has a value of 0; and wherein the generated Skin Attribute Index is indicative of skin inflammation.

The at least one color channel image may be a b-channel image; wherein the entropy value is a b-entropy value; wherein B, C, E each has a value of 0; and wherein the generated Skin Attribute Index is indicative of skin pigmentation or skin dullness.

The at least one color channel image may be a c-channel image; wherein the entropy value is a c-entropy value; wherein B, C, D each has a value of 0; and wherein the generated Skin Attribute Index is indicative of skin topography, which is preferably selected from the group consisting of: pores, fine lines, wrinkles, sagging, skin elasticity, and combinations thereof.

Obtaining Color Channel Image

The color channel image 60a, 60b, 60c may be obtained from a digital image 51 as described hereinafter with reference to FIGS. 5A, 5B, 5C and 6. Referring to FIG. 1, the network 100 may be used to acquire digital images from the portable electronic device 12 and transmitting the digital images to the apparatus 14 to be used in a method 200 for determining a cosmetic skin attribute according to the present invention. The input device 12a may be coupled to or integral with the portable electronic device 12 for receiving a user input for initiating the processor 14b. The portable electronic device 12 may comprise an output device 12b for displaying the plurality of tiles, each having uniquely assigned single degree of indicium. The input device 12a may include but is not limited to a mouse, a touch screen display, or the like.

Referring to FIGS. 1, 5A and 6, when the processor 14b is initiated, the processor 14b causes a digital image 51 of at least a portion of a face of the subject to be obtained, e.g. via image obtaining logic 144a in step 202. The obtained digital image 51 may be a RGB XP digital image or a RGB shine digital image. The digital image 51 in RGB system is converted from an RGB image to a digital image data, such as a color channel image in a different color system. The processor 14b further causes at least one color channel image 60a, 60b, 60c to be extracted, e.g. via image analysis logic 144b, from the obtained digital image 51 in step 204. The at least one color channel image may be a color channel image that is obtained by further processing of RGB color channels based on an equation, for example, 0.1R+0.2G+0.7B. The at least one color channel image 60a, 60b, 60c may be selected from any one of color channels 60a, 60b, 60c in a color system. In step 206, the extracted at least one color channel image 60a, 60b, 60c is filtered using a frequency filter. The filtered at least one color channel image 61a, 61b, 61c is analyzed using entropy statistics in step 208 to determine the cosmetic skin attribute of the person. Use of a frequency filter in step 206 removes noise from the extracted at least one color channel image 60a, which increases sensitivity of the analysis in step 208, thereby resulting in higher accuracy in an analysis output from step 208 relative to analyzing a non-filtered color channel image. However, analyzing a non-filtered color channel image may be advantageous to reduce usage in computing hardware, such as reducing hardware footprint, data storage space or processing capability in the event that only very minimal and basic hardware is available for implementing the methods according to the present invention.

Optionally, the method 200 may further comprise applying an image correction factor to the filtered color channel for optimizing parameters in the filtered color channel prior to analyzing the filtered color channel. The parameters may include illumination correction, blur correction, rotation correction or the like.

A technical effect of determining at least one skin attribute using the method 90, 200 according to the present invention is that it provides quick and accurate analysis of the cosmetic skin attributes. Table 3 below describes an age correlation with commonly used imaging end points and the correlation for entropy statistics have a better correlation (0.81) relative to the other imaging end points. Imaging end points may also be described as imaging methods for analyzing skin features.

TABLE 3

| Endpoint | Correlation |
| --- | --- |
| Texture area fraction | 0.43 |
| Spot area fraction | 0.55 |
| Wrinkle area fraction | 0.57 |
| L | −0.52 |
| a | 0.39 |
| b | 0.54 |
| L-Standard deviation | 0.02 |
| a-Standard deviation | 0.28 |
| b-Standard deviation | 0.35 |
| Haralick Contrast | 0.65 |
| Entropy Statistics | 0.81 |

The method 90, 200 may be performed in less than 5 seconds, preferably from 0.01 second to 5 seconds, more preferably from 0.5 seconds to 1 second, or different combinations of the upper and lower limits described above or combinations of any integer in the ranges listed above. As the method 90, 200 can be performed in less than 1 second, the method 200 may be implemented in commercially available hardware such as a portable handheld electronic device including but not limited to a mobile phone which is commercially advantageous because of its scalability to a wider network of consumers.

The color system may be an L*a*b color system and the at least one color channel image may be a red color channel 60a, a yellow color channel 60b or a blue color channel 60c corresponding a texture channel as shown in FIG. 5B. FIG. 5C shows the filtered color channel images 61a, 61b, 61c, each filtered color channel image is analyzed to obtain entropy values describing the analyzed color channel image. An entropy value of the filtered red color channel 61a may be defined as a-entropy, an entropy value of the filtered yellow color channel 61b may be defined as b-entropy and an entropy value of the filtered blue color channel 61c may be defined as c-entropy.

The color system may be a chromophore mapping space as described hereinbefore and the at least one color channel image may be a hemoglobin channel image or a melanin channel image.

The frequency filter may be a Fast Fourier transformation filter, a Wavelet transformation filter or a Difference of Gaussian (DoG) filter. More preferably, the frequency filter is a DoG filter. The DoG filter has a Gaussian filter 1 and a Gaussian filter 2. The Gaussian filter 1 may comprise a standard deviation from 1 to 200, from 5 to 50, from 10 to 20, different combinations of the upper and lower limits described above or combinations of any integer in the ranges listed above. The Gaussian filter 2 may comprise a standard deviation from 1 to 200, from 5 to 100, from 20 to 60, different combinations of the upper and lower limits described above or combinations of any integer in the ranges listed above. Non-limiting examples of combinations of Gaussian filter 1 and Gaussian filter 2 of the DoG filter are described in Table 4 below.

TABLE 4

| Gaussian Filter 1<br>Standard Deviation | Gaussian Filter 2<br>Standard Deviation |
| --- | --- |
| 1 to 200 | 1 to 200 |
| 5 to 50 | 5 to 100 |
| 10 to 20 | 20 to 60 |

The output device 12b may include but is not limited to a touch screen display, a non-touch screen display, a printer, a projector for projecting the plurality of tiles each having uniquely assigned single degree of indicium on a display surface such as for example a mirror as described hereinafter with respect to FIG. 2.

Figure 2:
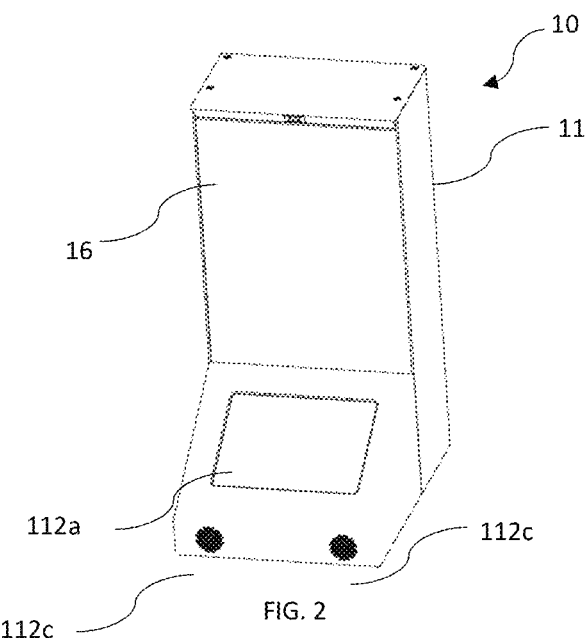
FIG. 2 is a diagram illustrating an alternative exemplary system for determining a cosmetic skin attribute according to the present invention.
Figure 3:
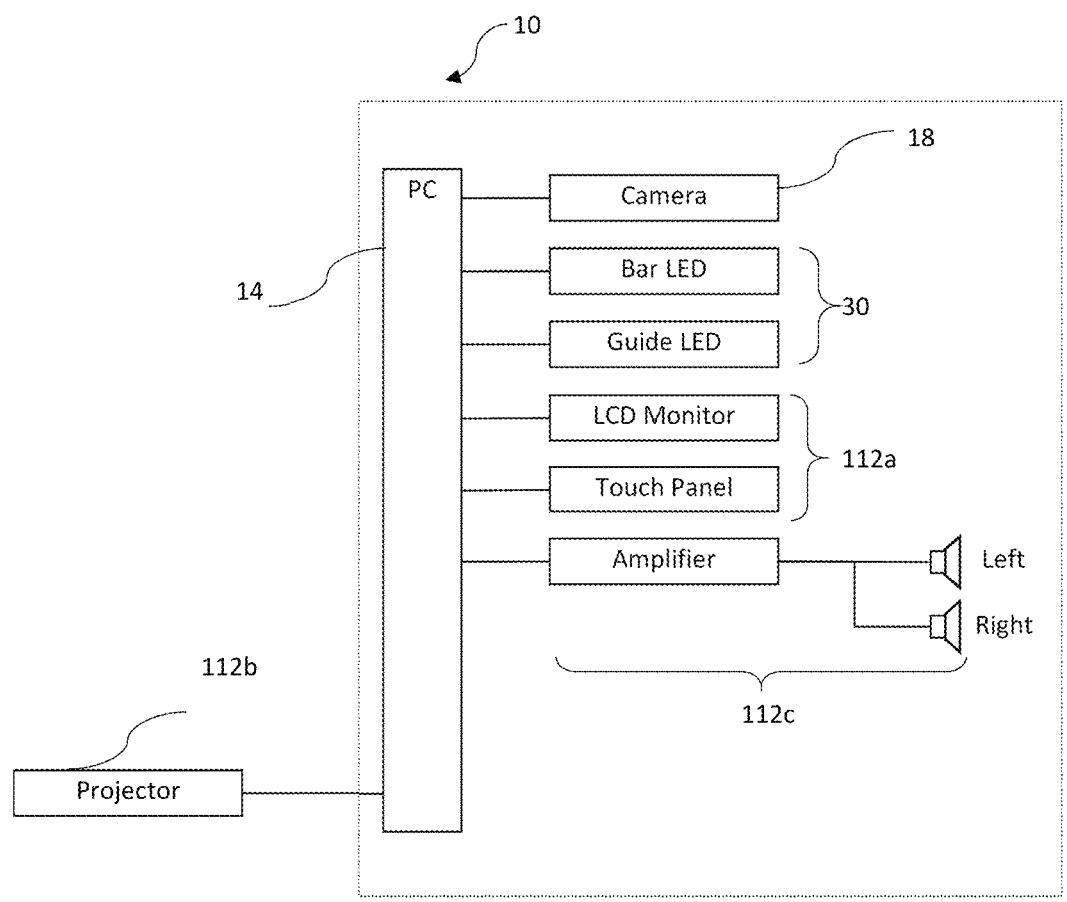
FIG. 3 is a block diagram illustrating components of an exemplary apparatus for determining a cosmetic skin attribute according to the present invention.

FIG. 2 is a perspective view of the system 10 configured as a stand-alone imaging system that is located at a retail cosmetics counter for the purpose of visualizing at least one cosmetic skin attribute and recommending cosmetic and skin care products based on the visualized at least one cosmetic skin attribute. FIG. 3 is a block diagram of the system 10 of FIG. 2. Referring to FIGS. 2 and 3, the system 10 comprises a housing 11 for the apparatus 14 of FIG. 1 connected to an image obtaining device 18 for acquiring a digital image of a subject for visualizing at least one cosmetic skin attribute. Referring to FIG. 2, the system 10 may comprise a mirror 16, and the image obtaining device 18 may be mounted behind the mirror 16 within the housing 11 so that the image obtaining device 18 may be hidden from view. The image obtaining device 18 may be a digital camera, an analog camera connected to a digitizing circuit, a scanner, a video camera or the like. The system 10 may include lights 30 such as LED lights arranged about the housing 11 to form an LED lighting system for assisting in generating a digital image of a subject. The system 10 has an input device 112a for receiving a user input. The system 10 may further comprise an output device 112b such as a projector configured to receive and project the facial map 30 for display on the mirror 16. The projector is not shown in FIG. 2 as it may be a peripheral component that is separate from the housing 11 but coupled to the apparatus 14 to form the system 10. The system 10 may further comprise a second output device 112c such as one or more speakers optionally coupled to an amplifier for generating audio guidance output to complement and/or enhance an overall consumer experience.

Preferably obtaining at least one color channel may comprise obtaining at least two color channels, more preferably three color channels. In particular, the red color channel, the yellow color channel and the blue color channel may be described as follows. When the red color channel is in the L*a*b* color system, a-entropy is an entropy value of the filtered red color channel. When the yellow color channel is in the L*a*b* color system, b-entropy is an entropy value of the filtered yellow color channel. When the blue color channel corresponds to a texture channel, c-entropy is an entropy value of the blue color channel.

The method 200 may further comprise a step of comparing at least one cosmetic attribute to a pre-defined dataset to assign an index. The index may be described as a Skin Attribute Index of the analyzed visually imperceivable consumer skin attribute, wherein the assigning a single degree of indicium uniquely to each tile is based on the assigned index. The plurality of tiles each having a uniquely assigned index may be displayed in a further step after the step of comparing.

Method of Visualizing Entropy Statistics

The present invention also relates to a method of visualizing entropy statistics or entropy values of at least one cosmetic skin attribute of at least a portion of a face of a subject in a digital image. The method is described with reference to FIGS. 8A and 8B which is a series of process flow diagrams illustrating how the entropy values are visualized, and FIG. 9 is a flow chart of a method 300 of visualizing entropy statistics or entropy values of at least one cosmetic skin attribute of at least a portion of a face of a subject in a digital image.

Figures 8A, 8B:
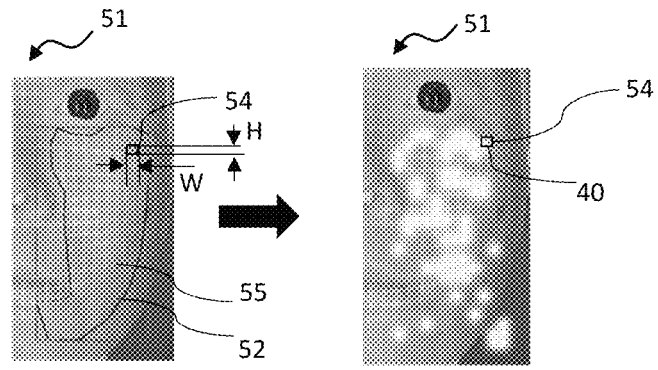
FIGS. 8A and 8B are process flow diagrams illustrating a method of visualizing entropy values of at least one cosmetic skin attribute of at least a portion of a face of a subject in a digital image according to the present invention.

A digital image 51 of at least a portion of the face is illustrated in FIG. 8A. The digital image 51 includes an area of the at least a portion of the face 1 defined by a boundary line 52 and comprises a plurality of tiles 54 across the digital image 51, each of the plurality of tiles 54 having at least one cosmetic skin attribute analyzed using entropy statistics. An outer periphery 53 envelopes the boundary line 52 surrounding the first digital image 51. The first digital image 51 is formed by a total number of pixels, for example, the first digital image 51 may have a number of pixels defining an overall image size of the first digital image 51. For example, if the tile size is set at 40 by 40 pixels to 70 by 70 pixels, accordingly, the number of tiles 54 that form the plurality of the tiles 54 across the first digital image 51 will be obtained by dividing the overall image size by the specified tile size. It will be appreciated that a size of the tile 54 may be defined by a number of pixels on a horizontal side (tile width, W) and a number of pixels on a vertical side (tile height, H). Each tile may comprise a tile size of not greater than 100 by 100 pixels, from 1 by 1 pixels to 100 by 100 pixels, from 2 by 2 pixels to 100 by 100 pixels, from 5 by 5 pixels to 90 pixels by 90 pixels, from 40 by 40 pixels to 70 by 70 pixels or different combinations of the upper and lower limits described above or combinations of any integer in the ranges listed above. A technical effect of having the tile size in the above ranges is that it enables a shorter processing time for analysis of the image data, and accordingly enable a display to visualize at least one cosmetic skin attribute in a shorter amount of time.

Figure 9:
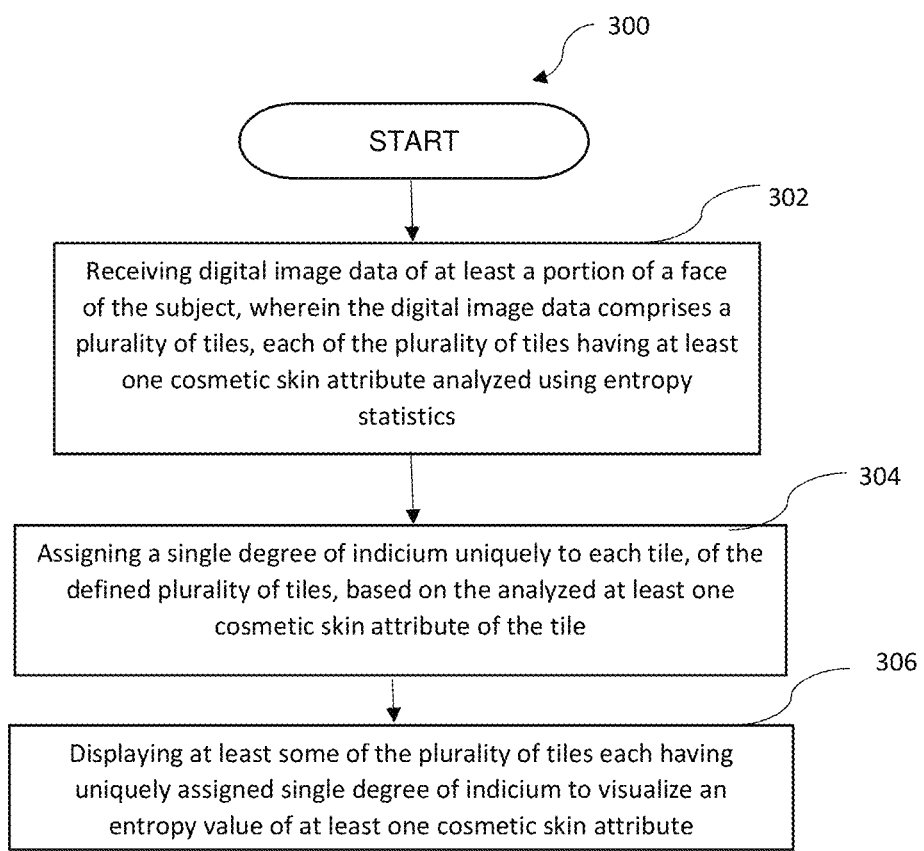
FIG. 9 is a flow chart illustrating a method of visualizing entropy values of at least one cosmetic skin attribute of at least a portion of a face of a subject in a digital image according to the present invention.

Referring to FIG. 9, the method 300 comprises receiving the digital image 51 in step 302 and in step 304, a single degree of indicium 40 is assigned uniquely to each tile 54 of the defined plurality of tiles based on the analyzed at least one cosmetic skin attribute. At least some of the plurality of tiles, each having uniquely assigned single degree of indicium are displayed in step 306 to visualize an entropy value of at least one cosmetic skin attribute as shown in FIG. 8B.

To explain the way the system 10 and the methods 90, 200, 300 work to determine and visualize at least one cosmetic skin attribute according to the present invention, it is helpful to understand how a digital image of a face of the subject is obtained in step 202, how the color channel image is extracted from the obtained digital image in step 204, how the extracted at least one color channel image is filtered in step 206, how a single degree of indicium is assigned uniquely to each tile in step 304 and how the tiles are displayed in step 306. Accordingly, the steps 202, 204, 206, 208 of the method 200 according to the present invention and the steps 302, 304 and 306 of the method 300 are described hereinafter as individual processes for performing each step. Each process may also be described as a subroutine, i.e. a sequence of program instructions that performs a corresponding step according to the methods 200, 300 according to the present invention.

Obtaining Digital Image

Figures 10A, 10B, 10C:
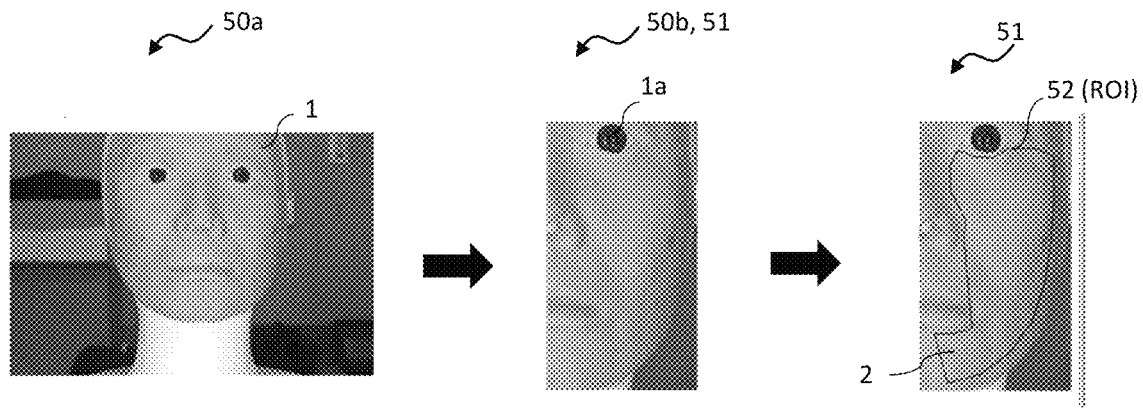
FIGS. 10A to 10C are a series of process flow diagrams illustrating details of a step of obtaining a first digital image in a method of determining a cosmetic skin attribute according to the present invention.
Figure 11:
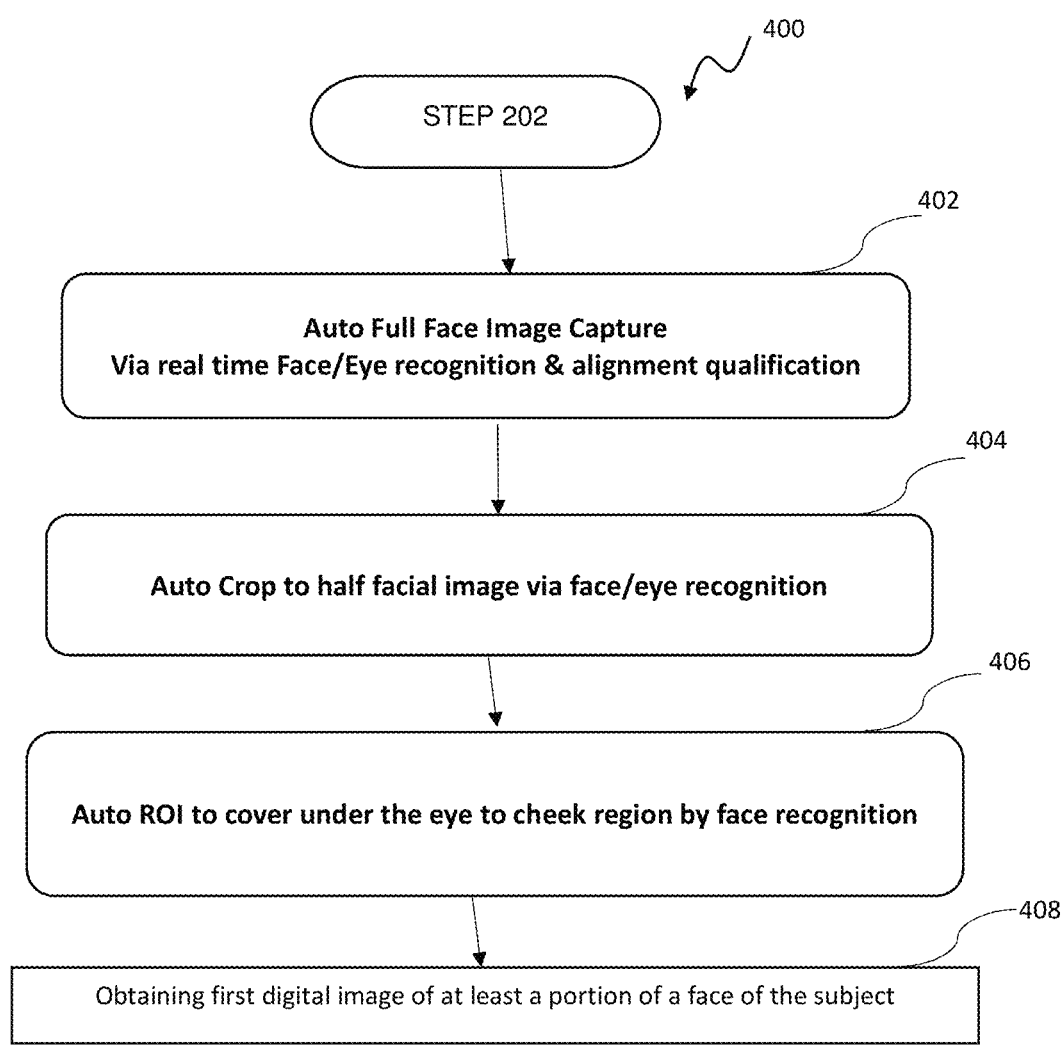
FIG. 11 is a flow chart illustrating the steps of obtaining the first digital image.

The step 202 of obtaining digital image according to the method 200 according to the present invention is described with reference to FIGS. 10A, 10B and 10C which is a series of process flow diagrams illustrating how digital image data is obtained from the digital image, and FIG. 11 is a flow chart of a process 400 of obtaining digital image data corresponding to the step 202.

An input image 50a of the face 1 is illustrated in FIG. 10A. The input image 50a may be captured by a user, for example, using the camera 18 in a step 402 of the process 400 as shown in FIG. 11. FIG. 10B illustrates a step 404 of cropping the input image 50a to obtain an edited image data 50b which comprises at least a portion of the face. The input image 50a may be cropped by identifying an anchor feature 1a of the face, including but not limited to facial features such as eyes, nose, nostrils, corners of the mouth or the like, and cropping accordingly. While the eye is depicted as the anchor feature 1a as shown in FIG. 10B, it will be appreciated that this is merely an example and any prominent or detectable facial feature(s) may be an anchor feature. The edited image data 50b may be a first digital image 51 that is obtained in step 404. Alternatively, as shown in FIG. 10C, the edited image data 50b may be further processed by cropping to remove one or more unwanted portions of the input image 50a thereby obtaining the first digital image data 51 which includes the at least a portion of the face 1 defined by a boundary line 52 in step 408. The obtained first digital image 51 may comprise at least one region of interest (ROI) 2 of the at least a portion of the face 1 that is defined by the boundary line 52. The ROI 2 may be the entire portion of the face 1, preferably at least a portion of the face, more preferably, one or more skin regions that defines the at least portion of the face 1. Details of how the skin regions are defined are described hereinafter with reference to FIGS. 14A to 14C, and the flowchart of FIG. 15.

Optionally, the process 400 may comprise step 406 in which the ROI 2 may be selected from the group consisting of: a skin region around the eye ("eye region 2a"), a skin region around the cheek ("cheek region 2b"), a skin region around the mouth ("mouth region 2c"), and combinations thereof, preferably the ROI 2 is a part of the at least a portion of the face 1 of the subject, more preferably the obtained first digital image data define a left or right side of the face 1. The ROI 2 may comprise an area of at least 5%, from 10% to 100%, from 25% to 90% of the obtained first digital image.

Defining Tiles

Figure 12:
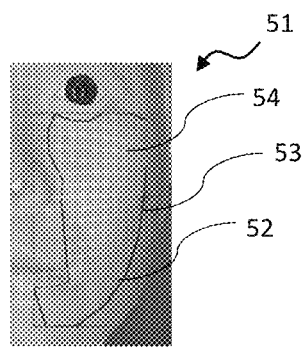
FIG. 12 is a picture illustrating a step of defining a plurality of tiles in in a method of determining a cosmetic skin attribute according to the present invention.
Figure 13:
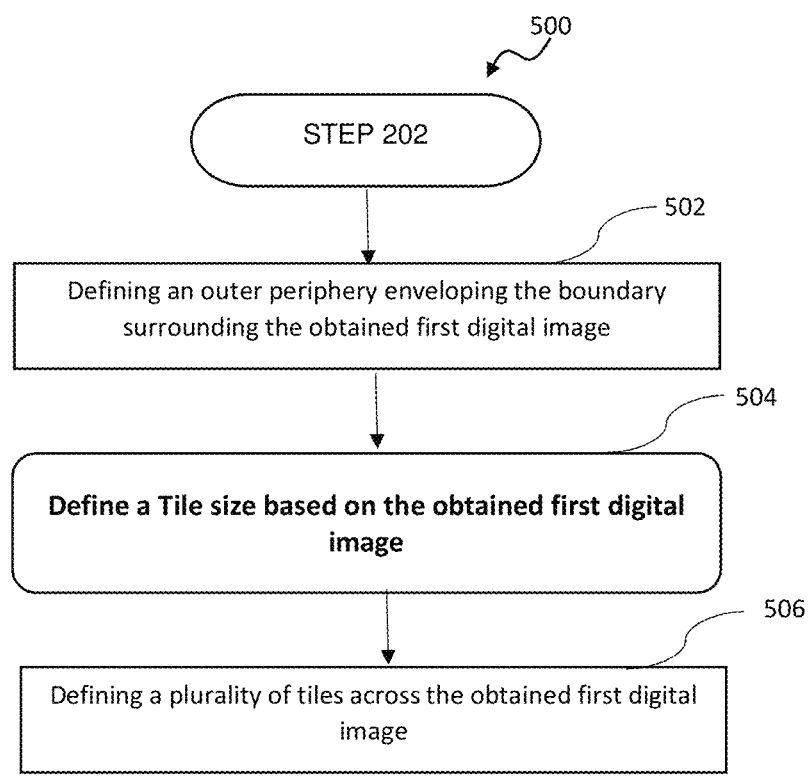
FIG. 13 is a flow chart illustrating the steps of defining the plurality of tiles.

FIG. 12 is a picture illustrating a plurality of tiles 54 on the first digital image data 51. FIG. 13 is a flow chart illustrating a process 500 of defining the plurality of tiles 54 on the first digital image data 51. Referring to FIG. 12, the first digital image 51 includes the at least a portion of the face 1 defined by a boundary line 52 as described hereinbefore with reference to FIG. 10C. Referring to FIG. 13, the process 500 comprises defining an outer periphery 53 enveloping the boundary line 52 surrounding the obtained first digital image (step 502). The obtained first digital image 51 is formed by a total number of pixels, for example, the obtained first digital image 51 may have a number of pixels which is determined at step 404 or step 406 depending an image size after cropping of the input image 50a. Accordingly, an overall image size based on the obtained first digital image 51 may be defined in step 504. For example, if the tile size is set at 40 by 40 pixels to 70 by 70 pixels, accordingly, the number of tiles 54 that form the plurality of the tiles 54 across the obtained first digital image 51 in step 506 will be obtained by dividing the overall image size by the specified tile size.

Displaying

Figure 21:
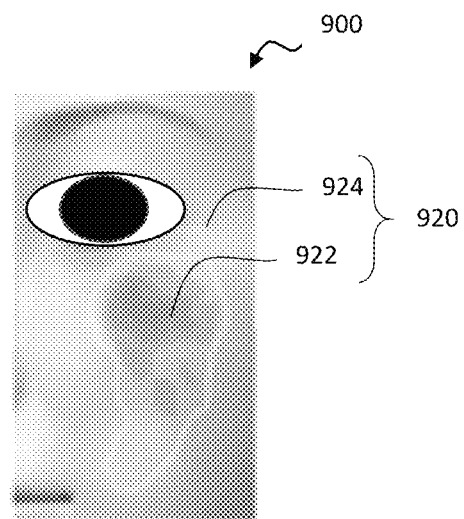
FIG. 21 is a screen shot illustrating an alternate variation of an image description for visualizing at least one cosmetic skin attribute in the user interface of FIG. 19.

The methods according to the present invention may further comprise a step of generating an image description corresponding to the generated Skin Attribute Index described hereinbefore for visualizing a cosmetic skin condition. The image description may comprise a heat map (such as shown in FIG. 8B, FIG. 21), an aggregate score (such as skin age shown in the fourth area 194 in FIG. 19D, feature 934 in FIG. 22), and combinations thereof. The aggregate score may be computed based on the generated Skin Attribute Index described hereinbefore.

FIGS. 14A to 14C are process flow diagrams illustrating details of a process of displaying a plurality of tiles according to step 306 of the method 300 of the present invention. FIG. 15 is a flow chart illustrating a process 600 of displaying the plurality of tiles. FIG. 14A is a picture illustrating a second digital image 60 interposed on the first digital image data 51. The second digital image 60 includes at least a portion of the face of the subject with displayed plurality of tiles 54 each having uniquely assigned single degree of indicium 40. FIG. 14B illustrates three zones, a first zone 110, a second zone 120, a third zone 130 displayed on the obtained first digital image based on the plurality of tiles 54 each having uniquely assigned single degree of indicium. Each zone 110, 120, 130 identifies a respective region of interest (ROI) 2 on the face 1 of the subject described hereinbefore with reference to FIGS. 9A to 9C and FIG. 10. FIG. 14C differs from FIG. 14B in that a boundary line 52 and an outer periphery 53 is displayed in the second digital image data 60 of FIG. 14B but are not displayed in the second digital image 60 of FIG. 14C. The first zone 110 may comprise a first zone line having a first zone color 110a, the second zone 120 may comprise a second zone line having a second zone color 120a and the third zone 130 may comprise a third zone line having a third zone color 130a. Based on the analyzed image data of the tiles 54 in each zone, a color of each zone lines may be different to better visually distinguish the tiles that visualize cosmetic skin attributes which may be in a normal, beautiful, or vulnerable condition relative to the other zones of the subject, such as for example as illustrated in an exemplary user interface of FIG. 19D.

FIG. 15 is a flow chart illustrating a process 600 of displaying the plurality of tiles in step 306 of the method 300 according to the present invention. The process 600 may begin in step 602 in which the processor reads analyzed image data of each tile 54 and assigns a single degree of indicium uniquely to each tile 54 of the plurality of tiles based on the analyzed at least one visually cosmetic skin attribute of the tile 54 (step 604). When the single degree of indicium is illumination, the analyzed image data of each of the tiles may be converted to reflect a corresponding degree of brightness of the illumination at each tile in step 606. In an exemplary example, the zone 110 may have a lower degree of illumination at each of the tiles within the zone 110 relative to a degree of illumination at each of the tiles within the zone 120. Further, in step 608, the zones may be defined such that the first zone 110 may correspond to an eye zone, the second zone 120 may correspond to a cheek zone and the third zone 130 corresponds to a mouth zone. An average index of the tiles of each zone may be calculated to generate a diagnosis of a skin condition correlating to a displayed cosmetic skin attribute according to the respective zone so as to assign a product recommendation item to the zone for treating the displayed cosmetic skin attribute in the zone.

Specifically, the method 300 may further comprise displaying at least one product recommendation item to treat the displayed cosmetic skin attribute.

Figure 16A:
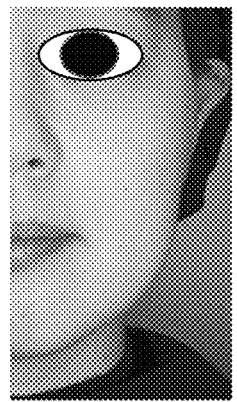
FIGS. 16A to 16D are process flow diagrams illustrating a method of visualizing entropy values of at least one cosmetic skin attribute according to the present invention.
Figure 16B:
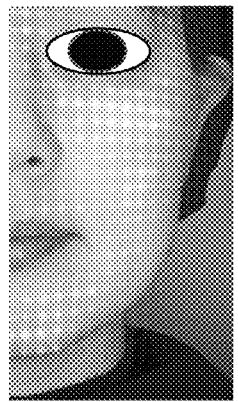
Figure 16C:
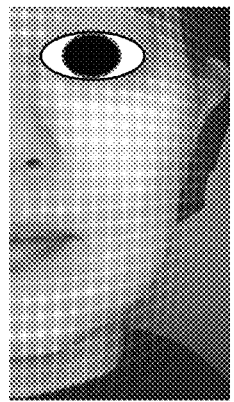
Figure 16D:
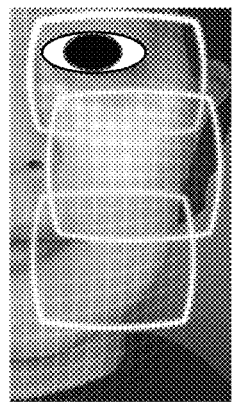
Figure 17:
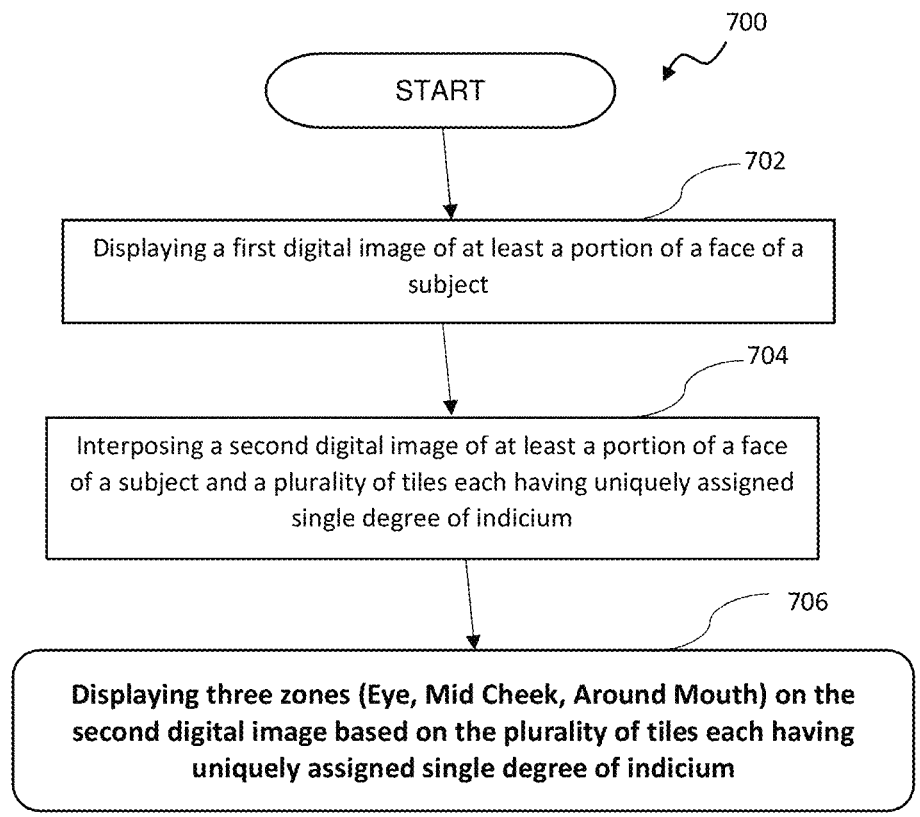
FIG. 17 is a flow chart illustrating a method of visualizing entropy values of at least one cosmetic skin attribute according to the present invention.

FIGS. 16A to 16D are process flow diagrams illustrating a method of visualizing at least one cosmetic skin attribute according to the present invention. FIG. 17 is a flow chart illustrating a method 700 of visualizing at least one cosmetic skin attribute according to the present invention. FIG. 16A is a color picture illustrating a first digital image of at least a portion of a face of a subject that is displayed in step 702 of the method 700 of FIG. 17. FIG. 16B is a color picture illustrating a second digital image of at least a portion of a face of a subject and a plurality of tiles each having uniquely assigned single degree of indicium, wherein the second digital image is interposed on the first digital image in step 704. Optionally, the first digital image may be converted into grey scale as shown in FIG. 16C to provide better contrast between the plurality of tiles each having uniquely assigned single degree of indicium and the first digital image. In step 706, three zones are displayed on the second digital image based on the plurality of tiles each having uniquely assigned single degree of indicium.

Figure 18:
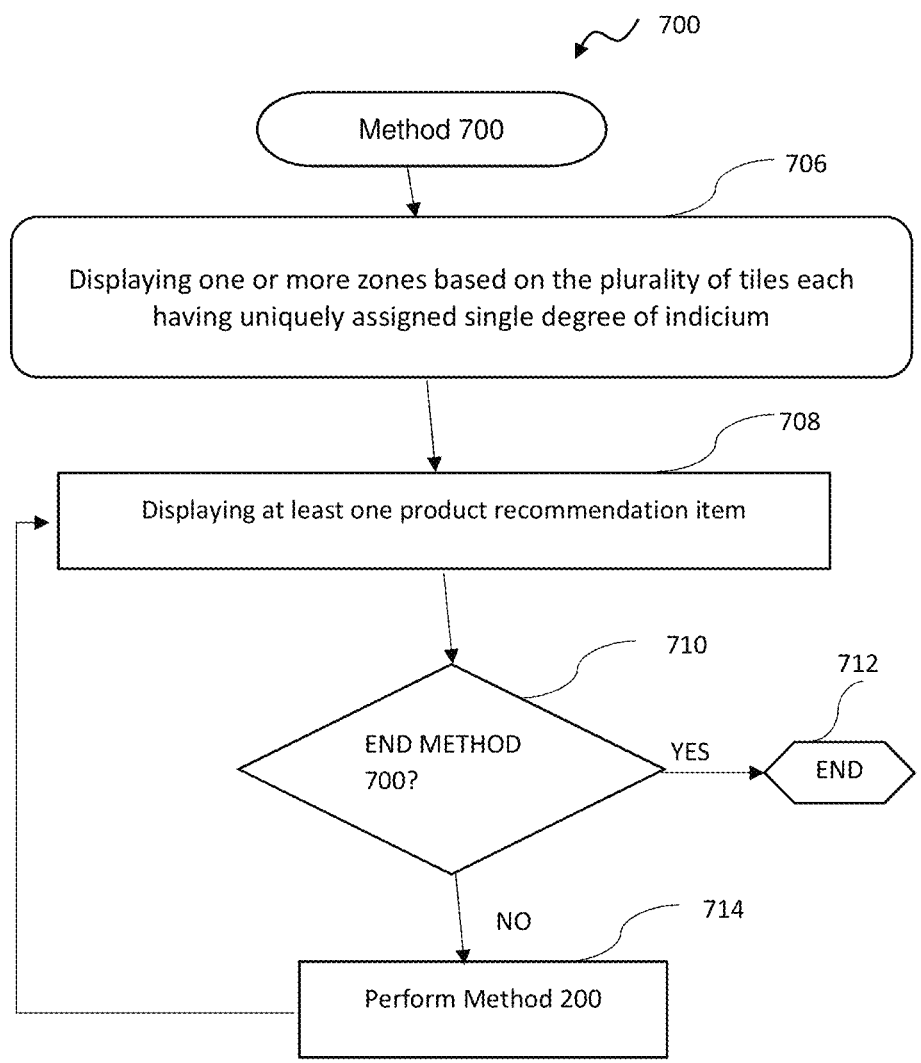
FIG. 18 is a flow chart illustrating an alternate method of visualizing entropy values of at least one cosmetic skin attribute according to the present invention.

FIG. 18 is a flow chart illustrating a variation of the method 700 of visualizing at least one cosmetic skin attribute as illustrated in FIG. 17. At least one product recommendation item is displayed in step 708 following step 706 of the method 700 of FIG. 17. In step 710, the user is prompted to select to end the method 700 and the method 700 terminates in step 712 if the user selects YES. If the user selects NO, steps of the method 200 of FIG. 6 is performed and the method 700 returns to step 708.

Human Machine User Interface

The present invention also relates to a human machine user interface (hereinafter "user interface") for providing a product recommendation to treat at least one cosmetic skin attribute. The user interface may be a graphical user interface on a portable electronic apparatus including a touch screen display/display with an input device and an image obtaining device. The user interface may comprise a first area of the touch screen display displaying a first digital image of at least a portion of a face of the subject obtained from the image obtaining device and a second digital image interposed on the first digital image, the second digital image having the at least a portion of a face of the subject and said displayed plurality of tiles each having uniquely assigned single degree of indicium. The user interface may further comprise a second area of the touch screen display different from the first area, the second area displaying a selectable icon for receiving a user input, wherein an image of at least one product recommendation item to treat the displayed cosmetic skin attribute is displayed on the touch screen display if the user activates the selectable icon.

FIGS. 19A to 19E are screen shots, each illustrating an exemplary user interface cooperating with each other for visualizing a cosmetic skin attribute according to the present invention. Although FIGS. 19A to 19E are described as a series of user interfaces which are provided in a sequential manner in response to a preceding user interface, it will be appreciated that the user interfaces of FIGS. 19A to 19E may be programmed in multiple ways to define an overall user interface for visualizing at least one cosmetic skin attribute according to methods according to the present invention as described hereinbefore. Preferably, all the user interfaces of FIGS. 19A to 19E define an exemplary user interface for visualizing a cosmetic skin attribute according to the present invention.

Figure 19A:
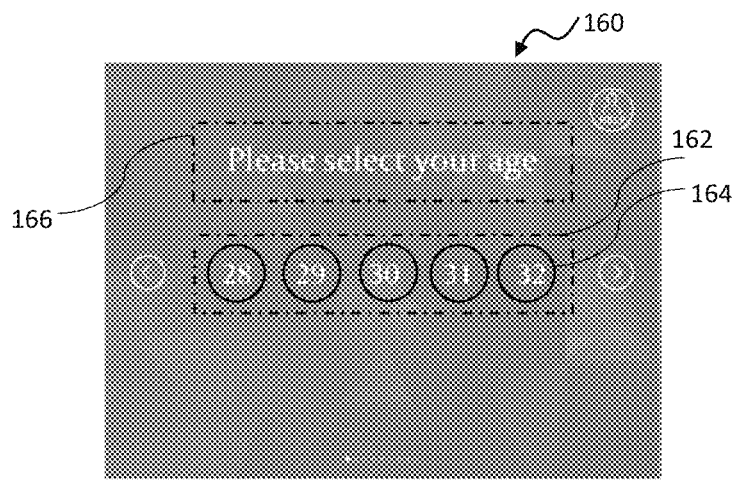
FIGS. 19A to 19E are screen shots, each illustrating an exemplary user interface for visualizing entropy values of at least one cosmetic skin attribute according to the present invention.

FIG. 19A depicts a user interface 160 for receiving a first user input, preferably the first user input is the age of the user. The user interface 160 may comprise a first area 162 for receiving the first user input. The first area 162 may include one or more user input features 164 for receiving the first user input. The user input feature 164 may be such as for example, a selectable input icon corresponding to a predetermined user feature such as for example a user's age as shown in FIG. 19A. The user interface 160 may further comprise a second area 166 including corresponding instructions to the user for providing the first user input. The second area 166 may be disposed above the first area 162 so as to be provide a more user-friendly interface. The user interface 160 may be part of a start option for beginning a method 200 according to the present invention.

Figure 19B:
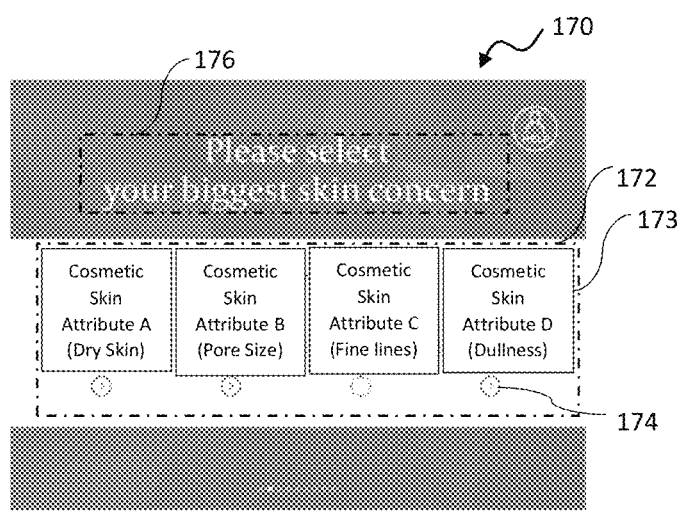

FIG. 19B depicts a user interface 170 for receiving a second user input, preferably the second user input is a cosmetic skin attribute that is causing concern to the user. The cosmetic skin attribute may be described as a skin concern of the user. The user interface 170 may be provided in response to the selection of a first user input from the user input feature 164 of FIG. 19A. The user interface 170 may comprise a first area 172 for receiving the second user input. The first area 172 may include one or more user input features 174 for receiving the second user input. The user input feature 174 may be such as for example, a selectable input icon corresponding to a predetermined skin concern. The first area 172 may further comprise an explanatory area 173 corresponding to the one or more input features 174 in which the explanatory area 173 includes a brief description of a cosmetic skin attribute or the skin concern. The user interface 170 may further comprise a second area 176 including corresponding instructions to the user for providing the user input. The second area 176 may be disposed above the first area 172 so as to be provide a more user-friendly interface.

Figure 19C:
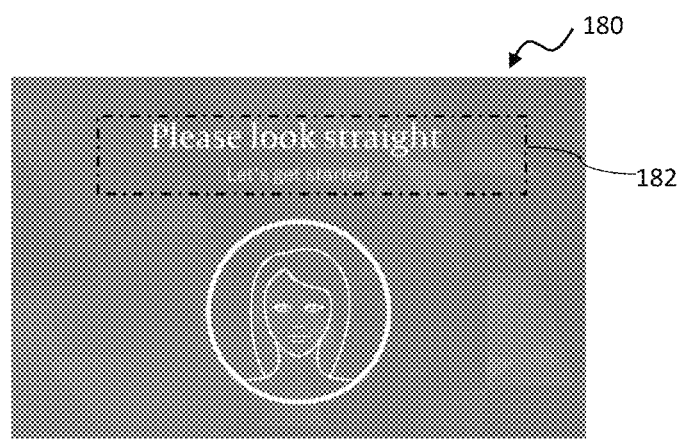

FIG. 19C depicts a user interface 180 for obtaining an input image of a user. The user interface 180 may comprise a first area 182 with instructions for aligning an anchor feature (such as eyes) so as to obtain the first digital image data according to the process 400 as described in FIG. 11. The user interface 180 may be provided in response to the selection of the second user input through the one or more user input features 174 of FIG. 19B.

Figure 19D:
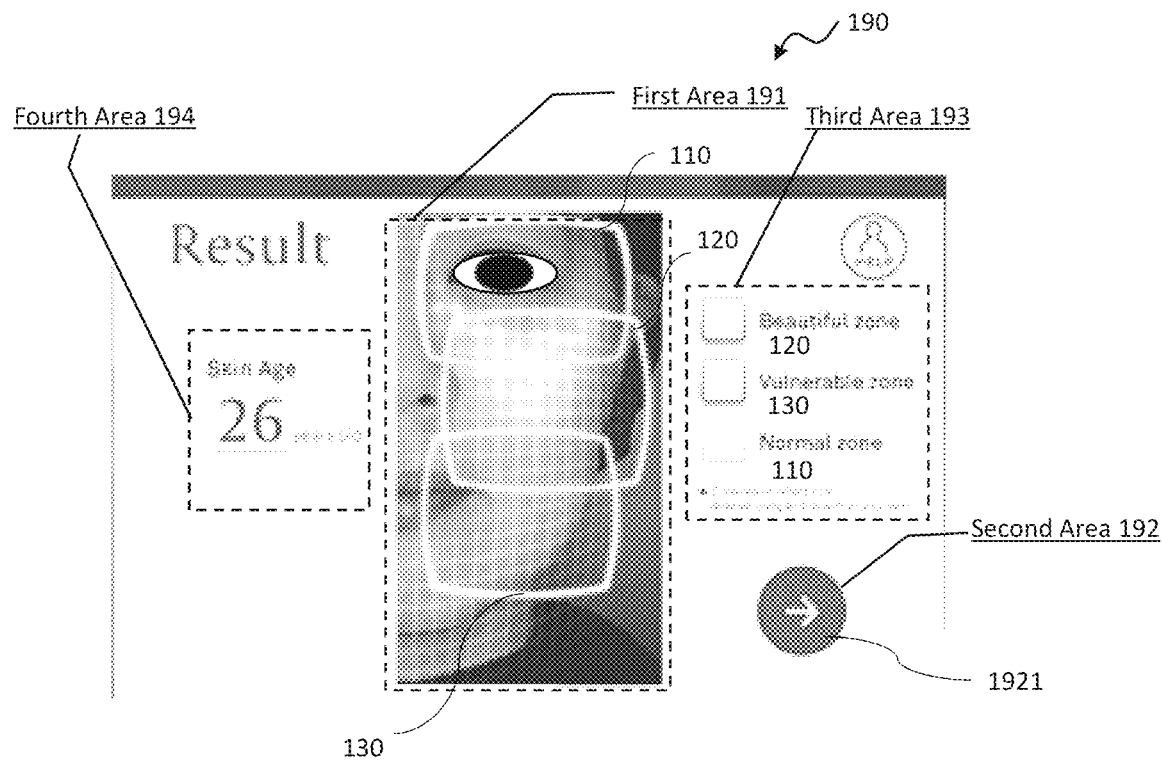

FIG. 19D depicts a user interface 190 for displaying at least one cosmetic skin attribute. The user interface 190 may be provided after the input image of the user is obtained in the user interface 180 of FIG. 19C. As shown in FIG. 19D, the at least one portion of skin of the person is facial skin; wherein the facial skin comprises at least one region of interest (ROI), which is preferably selected from the group consisting of cheek region/zone, eye region/zone, forehead region/zone, nose region/zone, and combinations thereof; and wherein the image description visualizes a need for improvement in said at least one ROI or a difference in the cosmetic skin attribute between a first ROI and a second ROI.

The user interface 190 may comprise a first area 191 displaying the plurality of tiles each having uniquely assigned single degree of indicium to visualize at least one cosmetic skin attribute according to methods of the present invention. The first area 191 may display similar features as shown in FIG. 18D but differs only in that lines defining the plurality of tiles may be turned off and/or set as an invisible layer. The first area 191 may comprise a first zone 110 corresponding to an eye zone of the at least a portion of the face of the user, a second zone 120 corresponding to a cheek zone of the at least a portion of the face of the user, and a third zone 130 corresponding to a mouth zone of the at least a portion of the face of the user. As shown in FIG. 19D, a zone result may be displayed in a third area 193 whereby the zone result comprises an index which may be generated for each zone based on a relative comparison of the indexes of the zones within the at least a portion of the face of the user. In an exemplary embodiment, depending on the zone results, the first zone 110 may be described as a normal/beautiful/vulnerable zone, the second zone 120 may be described as a normal/beautiful/vulnerable zone and the third zone 130 may be described as a normal/beautiful/vulnerable zone. Preferably, each zone may have different descriptions based on the relative differences in the zone results. The user interface 190 also includes a second area 192 for receiving a third user input. The second area 192 may include one or more user input features 1921 for receiving the third user input. The user input feature 1921 may be such as for example, a selectable input icon for proceeding with a next step of the method according to the present invention. Optionally, the user interface 190 may comprise a fourth area 194 for displaying a skin age of the user based on the analyzed at least one cosmetic skin attribute of each tile of the plurality of tiles based on the obtained first digital image data of the at least a portion of the face of the user.

Figure 19E:
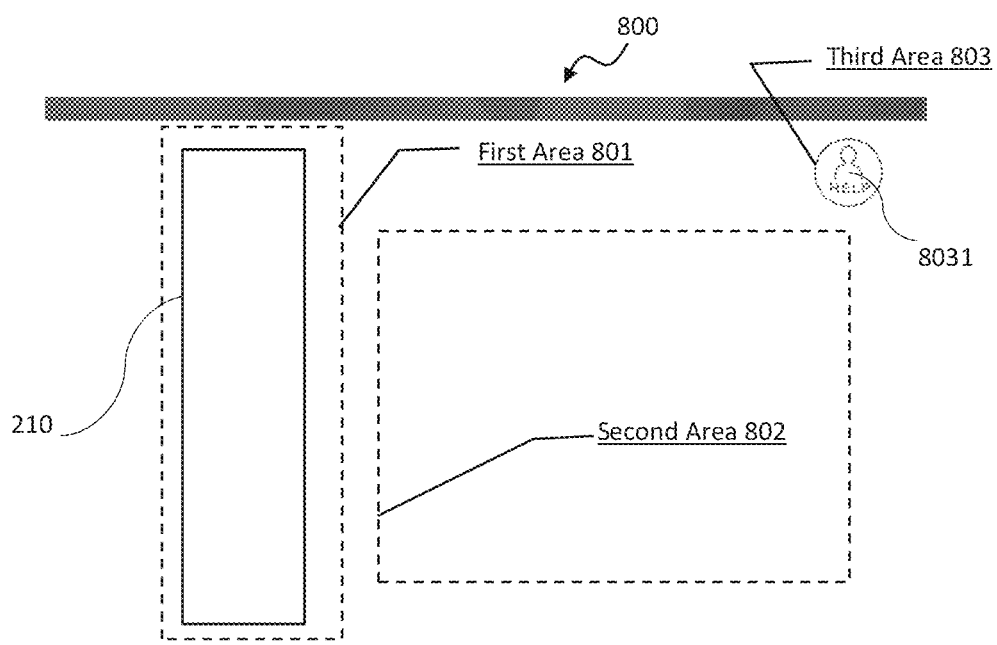

FIG. 19E depicts a user interface 800 comprising a first area 801 for displaying a product recommendation item 210. The user interface 800 may be provided in response to selection of the user input feature 1921 from the user interface 190 of FIG. 19D. Optionally, the user interface 800 may comprise a second area 802 for providing details of the product recommendation item 210. Preferably, the user interface 800 may comprise a third area 803 for receiving a fourth user input such as for example request for assistance from a product consultant for enquiry and/or purchase of the product recommendation item 210. The third area 803 may include one or more user input features 2031 for receiving the fourth user input. The user input feature 2031 may be such as for example, a selectable input icon for proceeding with a next step of the method according to the present invention.

Figure 20:
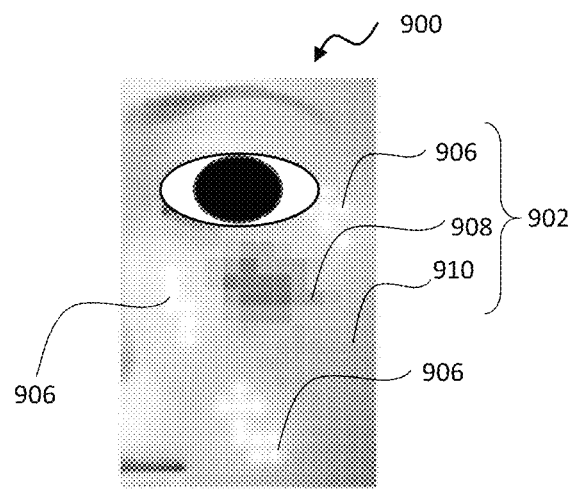
FIG. 20 is a screen shot illustrating an exemplary user interface comprising a heat map as an example of an image description for visualizing at least one cosmetic skin attribute according to the present invention.

FIG. 20 depicts a partial view of an exemplary user interface 900 comprising an image description 901 overlaid on a digital image 51 for visualizing at least one cosmetic skin attribute according to the present invention. The image description 902 comprises a heat map generated based on the entropy values output from the method 90 described hereinbefore. The heat map comprises a first heat map section 906 based on low entropy values which correspond to a better cosmetic skin attribute condition. The heat map 904 further comprises a second heat map section 908 based on high entropy values correspond to a poorer cosmetic skin attribute condition. The first heat map section 906 is formed of a first plurality of tiles which is visually different from a second plurality of tiles in the second heat map section 908. For example, the first plurality of tiles is converted to display a different color from the color of the second plurality of tiles. Heat map sections 910 which are not displayed (hereinafter "non-displayed heat map sections 910") correspond to entropy values between the high and low entropy values. The heat map sections may be configured as follows to display entropy information related to the cosmetic skin attribute condition and the Skin Attribute Index as outlined in Table 5 below.

TABLE 5

| Heat Map | Heat Map Section Visualization | Entropy Values | Cosmetic Skin Attribute Condition |
| --- | --- | --- | --- |
| Heat Map Section 906 | Displayed as first color | Low | Better |
| Heat Map Section 908 | Displayed as second color different from first color | High | Poor |
| Heat Map Section 910 | Not Displayed | Between Low and High | Between Poor and Better |

FIG. 21 depicts an alternate variation of an image description 920 for visualizing at least one cosmetic skin attribute in the user interface 900 of FIG. 19. The image description 920 differs from the image description 902 of FIG. 19 in that the image description 920 comprises a displayed region of interest (ROI) 922 wherein the displayed ROI 922 is converted to display a color to indicate poorer cosmetic skin attribute condition relative to other non-displayed regions of interest (ROI) 924 which correspond to better cosmetic skin attribute condition. An advantage of only displaying a single heat map section (see FIG. 20) or ROI is that the consumer viewing the user interface is not overloaded with too much visual information.

Figure 22:
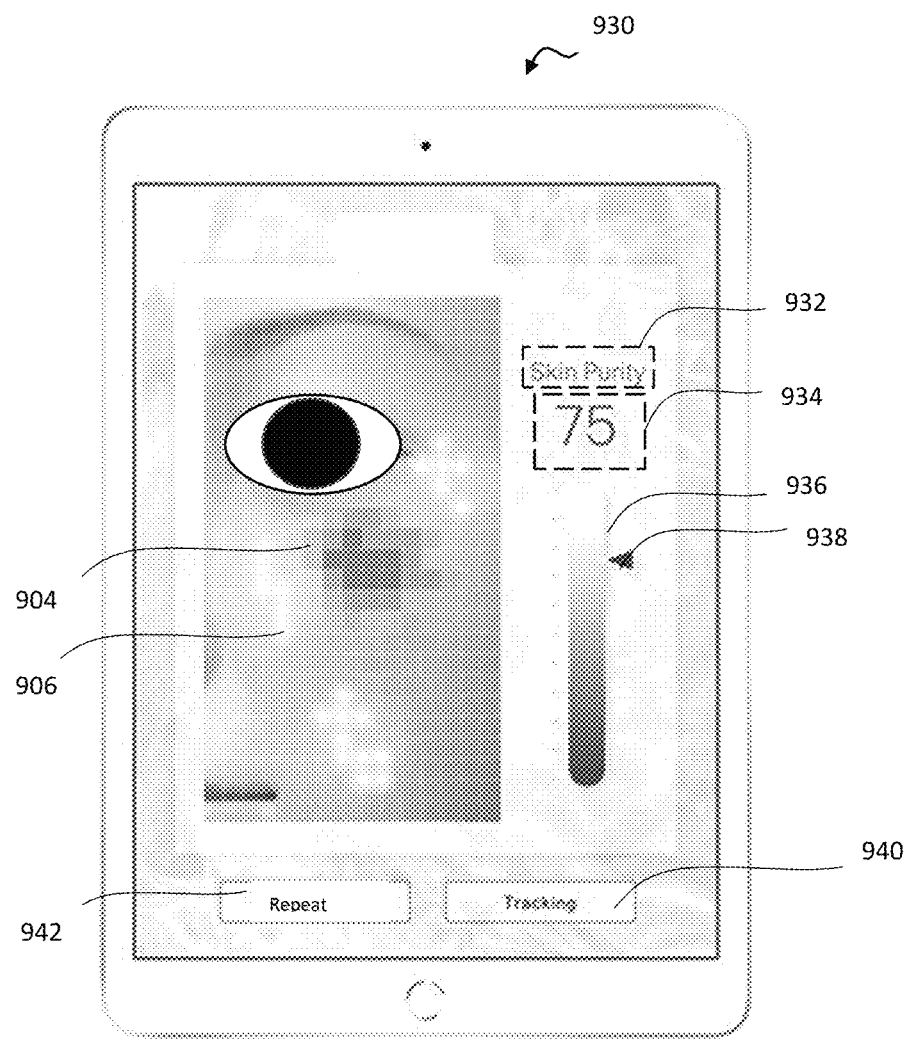
FIG. 22 is a screen shot illustrating an exemplary user interface for visualizing at least one cosmetic skin attribute according to the present invention.

FIG. 22 is a screen shot illustrating an exemplary user interface 930 for visualizing at least one cosmetic skin attribute according to the present invention, wherein the at least one cosmetic skin attribute is skin purity. The user interface 930 differs from the user interface 902 of FIG. 19 in that the user interface 930 comprises alternate text 932 describing the cosmetic skin attribute and an aggregate score 934 based on the generated Skin Attribute Index. The user interface 930 may further comprise a meter 936 and a meter marker 938 for representing the aggregate score on a scale of 0 to 100 along the meter 936. The meter 936 is a different way of visualizing the aggregate score 934, and may be optional. A color of the meter 936 may be configured to show a gradient of colors representative of the first heat map section 904 and the second heat map section 906.

The methods for determining a cosmetic skin condition according the present invention described hereinbefore may further comprise a step of tracking the cosmetic skin attribute over a predetermined period of time. For example, the user interface 930 as shown in FIG. 21 may comprise a first selectable icon 940 which upon selection, causes instructions to be received by and steps performed by the processor to generate a calendar or schedule to create a cosmetic skin attribute diary to track improvement of cosmetic skin attributes. For example, when the consumer uses it on Day 1, the date and facial analysis is recorded and saved in the memory. Subsequently, whenever the consumer uses the method according to the present invention in future (after a predetermined period, 1 week, 1 month, 6 months), the facial skin of the consumer is analyzed again and the consumer can compare how his/her facial skin looks at the time after the predetermined period relative to Day 1. The methods according to the present invention may be configured to be a downloadable software application that is stored as a native application on a portable electronic device or a web application that can be accessed through a login account specific to a consumer, so that the consumer can perform a self-skin analysis based on the methods according to the present invention and view and/or monitor the improvement (reduction in the ROIs with poorer cosmetic skin attribute condition) over a period of time.

The user interface 930 may further comprise a second selectable icon 942 which upon selection, enables the method for determining a cosmetic skin attribute according to the present invention to be repeated. For example, the method 90 described hereinbefore may be repeated.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of determining a cosmetic skin attribute of a person, the method comprising:
   a) obtaining at least one color channel image comprising at least one portion of skin of the person;
   b) analyzing the at least one color channel image using entropy statistics to obtain an entropy value; and
   c) determining the cosmetic skin attribute of the at least one portion of skin of the person based on the entropy value;
   wherein a Skin Attribute Index is generated as a probability value indicative of a condition of the cosmetic skin attribute of the at least one portion of skin of the person relative to a defined population of people;
   wherein the Skin Attribute Index is generated as a function of the entropy value defined by F(Entropy Value), wherein said function is determined by a model established upon a training dataset wherein the training dataset comprises (i) a plurality of color channel images of a the defined population of people, wherein each of the plurality of color channel images comprises facial skin of a person in the defined population of people, wherein the facial skin comprises the cosmetic skin attribute, and (ii) an associated class definition based on the cosmetic skin attribute;
   wherein the at least one color channel image is an image in the L*a*b* color system selected from the group consisting of an L-channel image, an a-channel image, a b-channel image and a c-channel image from RGB color system, and combinations thereof; wherein the entropy value is selected from the group consisting of a L-entropy value, an a-entropy value, a b-entropy value, a c-entropy value, and combinations thereof; and wherein the function has the formula: Skin Attribute Index=A+B×(L-entropy value)+C×(a-entropy value)+D×(b-entropy value)+E×(c-entropy), wherein A, B, C, D, and E are constants; wherein at least one of B, C, D, and E is not 0.

2. The method according to claim 1, wherein the at least one color channel image is an L-channel image; wherein the entropy value is an L-entropy value; wherein C, D, and E each have a value of 0; and wherein the generated Skin Attribute Index is indicative of skin purity, skin tone or skin radiance.

3. The method according to claim 1, wherein the at least one color channel image is an a-channel image, the entropy value is an a-entropy value, and B, D, and E each have a value of 0, and wherein the generated Skin Attribute Index is indicative of skin inflammation.

4. The method according to claim 1, wherein the at least one color channel image is a b-channel image, the entropy value is a b-entropy value, and B, C, and E each have a value of 0, and wherein the generated Skin Attribute Index is indicative of skin pigmentation or skin dullness.

5. The method according to claim 1, wherein the at least one color channel image is a c-channel image, the entropy value is a c-entropy value, and B, C, and D each have a value of 0, and wherein the generated Skin Attribute Index is indicative of skin topography.

6. The method of claim 5, wherein the skin topography is selected from the group consisting of pores, fine lines, wrinkles, sagging, skin elasticity, and combinations thereof.

7. The method of claim 1, further comprising generating and displaying an image description corresponding to the generated Skin Attribute Index.

8. The method of claim 1, wherein the model is a regression model or a classification model.

9. The method of claim 8, wherein said regression model is a regression model selected from the group consisting of a linear regression model, a machine learning linear regression model, a machine learning support vector regression model, or a random forest regression model.

10. The method according to claim 1, wherein the cosmetic skin attribute is selected from the group consisting of skin purity, skin age, skin topography, skin tone, skin pigmentation, skin pores, skin inflammation, skin hydration, skin sebum level, acne, moles, skin radiance, skin shine, skin dullness, and skin barrier.

11. The method according to claim 10, wherein the cosmetic skin attribute is a visually imperceivable cosmetic skin attribute, wherein the visually imperceivable cosmetic skin attribute is a cosmetic skin attribute which is not detectable by an unaided eye, or a cosmetic skin attribute detectable visually by a consumer but the consumer does not understand the cosmetic skin attribute.

12. The method of claim 1, wherein prior to analyzing, the at least one color channel image is filtered by using a frequency filter selected from the group consisting of Fourier Transformation Filter, Wavelet Transformation, and Difference of Gaussian (DoG) filter.

13. The method of claim 12, wherein the first Gaussian Filter has a standard deviation of 5 to 50 and the second Gaussian filter has a standard deviation of 5 to 100.

14. The method of claim 1, wherein the at least one portion of skin of the person is facial skin; wherein the facial skin comprises at least one region of interest (ROI) selected from the group consisting of cheek region, eye region, forehead region, nose region, and combinations thereof, and wherein the image description displays a need for improvement in said at least one ROI or a difference in the cosmetic skin attribute between a first ROI and a second ROI.

* * * * *